US008889863B2

(12) United States Patent
Johnston et al.

(10) Patent No.: US 8,889,863 B2
(45) Date of Patent: Nov. 18, 2014

(54) STEREOSELECTIVE METHODS, CATALYSTS AND INTERMEDIATES FOR THE SYNTHESIS OF (−)-NUTLIN-3 AND RELATED COMPOUNDS

(75) Inventors: Jeffrey N. Johnston, Nashville, TN (US); Tyler A. Davis, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 0 days.

(21) Appl. No.: 13/183,202

(22) Filed: Jul. 14, 2011

(65) Prior Publication Data

US 2012/0088915 A1    Apr. 12, 2012

Related U.S. Application Data

(60) Provisional application No. 61/365,124, filed on Jul. 16, 2010.

(51) Int. Cl.
| | | |
|---|---|---|
| *C07C 233/64* | (2006.01) | |
| *C07D 241/08* | (2006.01) | |
| *C07D 401/14* | (2006.01) | |
| *C07C 269/06* | (2006.01) | |
| *C07D 403/06* | (2006.01) | |
| *C07C 271/14* | (2006.01) | |
| *C07D 215/42* | (2006.01) | |

(52) U.S. Cl.
CPC ............ *C07C 269/06* (2013.01); *C07D 403/06* (2013.01); *C07C 271/14* (2013.01); *C07D 215/42* (2013.01)
USPC ............................ 544/384; 546/163; 564/179

(58) Field of Classification Search
USPC ............................ 544/384; 564/179; 546/163
See application file for complete search history.

(56) References Cited

U.S. PATENT DOCUMENTS

| | | | | |
|---|---|---|---|---|
| 6,835,371 | B1 | 12/2004 | Elmaleh et al. | 424/9.1 |
| 2005/0282803 | A1 | 12/2005 | Hayley et al. | 514/227.5 |

OTHER PUBLICATIONS

Petrini et al. (Tetahedron Letters 47 (2006); p. 3501-3503).*
Bloom et al. (J. Chem. Soc., Perkin Trans. 1: Organic and Bio-Organic Chemistry (1984), (10); p. 2357-2362).*
Drefahl et al. (Chemische Berichte (1960), 93, p. 500-505).*
Adams et al.,"The nitro-Mannich reaction and its application to the stereoselective synthesis of 1,2-diamine," *J. Org. Chem.*, 63:9932-9934, 1998.
Akiyama et al., "Recent progress in Chiral Brønsted acid catalysis," *Advanced Synth. Catalysis*, 348:999-1010, 2006.
Bernardi et al., "Enantioselective aza-Henry reaction using cinchona organocatalysts," *Tetrahedron*, 62:375-380, 2005.
Bond et al., "MDM2 is a central node in the p53 pathway: 12 years and counting," *Curr. Cancer Drug Targets*, 5:3-8, 2005.

Cardona and Goti, "Metal-catalysed 1,2-diamination reactions ," *Nat. Chem.*, 1:269-275, 2009.
Carvajal et al., "Activation of p53 by MDM2 antagonists can protect proliferating cells from mitotic inhibitors ," *Cancer Res.*, 65:1918-1924, 2005.
Davis and Johnston, "Catalytic, enantioselective synthesis of stilben *cis*-diamines: A concise preparation of (−)- Nutlin-3, a potent p53/MDM2 inhibitor," *Chem. Sci.*, 2:1076-1079, 2011.
Davis et al., "Bifunctional asymmetric catalysis: Amplification of Brønsted basicity can orthogonally increase the reactivity of a chiral brønsted acid," *J. Am. Chem. Soc.*, 132:2880-2882, 2010.
Faugeroux and Genisson, "The Imino-pinacol Coupling Reaction," *Curr. Organic Chem.*, 12:751-773, 2008.
Fini et al., "Phase-Transfer-Catalyzed Asymmetric Aza-Henry Reaction Using N-Carbamoyl Imines Generated In Situ from -Amido Sulfones," *Angew. Chem. Int. Ed.*, 44:7975-7978, 2005.
Fischer and Lane, "Small-molecule inhibitors of the p53 suppressor HDM2: have protein-protein interactions come of age as drug targets?," *Trends Pharmacol. Sci.*, 25:343-346, 2004.
Fry et al., "Development of E3-substrate (MDM2-p53)-binding inhibitors: structural aspects," *Methods Enzymol.*, 399:622-633, 2005.
Fry et al., "Exploiting protein-protein interactions to design and activator of p53," *Protein-Protein Interact.*, 2nd Ed., 893-906, 2005.
Harris, "Protein-protein interactions for cancer therapy," *Proc. Natl. Acad. Sci. USA*, 103:1659-1660, 2006.
Hattori et al., "Synthesis, resolution, and absolute stereochemistry of (−)- blestriarene C," *J. Org. Chem.*, 68:2099-108, 2003.
Hendrickson and Hussoin, "Reactions of carboxylic acids with phosphonium anhydrides," *J. Org. Chem.*, 54:1144-1149, 1989.
Hendrickson and Hussoin, "Seeking the ideal dehydrating reagent," *J. Org. Chem.*, 52:4137-4139, 1987.
Hendrickson and Schwartzman, "Triphenyl phosphine ditriflate: A general oxygen activator," *Tetrahedron Lett.*, 16:277-280, 1975.
Kanazawa et al., "Highly stereocontrolled and efficient preparation of the protected, esterification-ready docetaxel (taxotere) side chain," *J. Org. Chem.*, 59, 1238-1240, 1994.
Kim et al., "Preparation of chiral diamines by the diaza-cope rearrangement (DCR)," *Aldrichimica Acta*, 41:77-88, 2008.
Knudsen et al., "The first catalytic asymmetric Aza-Henry reaction of nitronates with imines: A novel approach to optically active β-nitro-α-amino acid- and α,β-diamino acid derivatives," *J. Am. Chem. Soc.*, 123:5843-5844, 2001.
Kornblum et al., "A new method for the synthesis of aliphatic nitro compounds," *J. Am. Chem. Soc.*, 78:1497-1501, 1956.
Lowe et al., "Intrinsic tumour suppression," *Nature*, 432:307-315, 2004.
Lucet et al., "The Chemistry of Vicinal Diamines,"*Angew. Chem. Int. Ed.*, 37:2580-2627, 1998.
Marianacci et al., "Organocatalytic asymmetric Mannich reactions with N-Boc and N-Cbz protected alpha-amido sulfones (Boc: tert-butoxycarbonyl, Cbz: benzyloxycarbonyl)," *Chemistry*, 13:8338-8351, 2007.
Marques-Lopez et al., "Catalytic enantioselective Aza-Henry reactions," *Eur. J. Org. Chem.*, 2401-2420, 2009.

(Continued)

*Primary Examiner* — Kristin Vajda
*Assistant Examiner* — Valerie Rodriguez-Garcia
(74) *Attorney, Agent, or Firm* — Parker Highlander PLLC

(57) ABSTRACT

The present invention provides methods and intermediates are provided for the preparation of (−)-Nutlin-3. Methods and intermediates are also provided for the enantioselective addition of aryl nitromethanes to aldimines. Bis(amidine) catalysts for the use in these and other reactions are also provided.

14 Claims, 10 Drawing Sheets

(56) References Cited

OTHER PUBLICATIONS

Mortensen and O'Doherty, "Recent advances in 1,2-diamination of alkenes," *Chemtracts*, 18:555-561, 2005.

Nugent et al., "Chiral proton catalysis: a catalytic enantioselective direct aza-Henry reaction," *J. Am. Chem. Soc.*, 126:3418-3419, 2004.

Okino et al., "Enantioselective aza-Henry reaction catalyzed by a bifunctional organocatalyst," *Org. Lett.*, 6:625-627, 2004.

Palomo et al., "Catalytic enantioselective aza-Henry reaction with broad substrate scope," *J. Am. Chem. Soc.*, 127:17622-17623, 2005.

Pemberton et al., "Synthesis and evaluation of dihydroimidazolo and dihydrooxazolo ring-fused 2-pyridones—targeting pilus biogenesis in uropathogenic bacteria," *Tetrahedron* 64:9368-76, 2008.

Petersson et al., "The structure of polymer-supported triphenylphosphine ditriflate: a potentially useful reagent in organic synthesis," *J. Org. Chem.*, 73:4691-4693, 2008.

Petersson et al., "The use of phosphonium anhydrides for the synthesis of 2-oxazolines, 2-thiazolines and 2-dihydrooxazine under mild conditions," *Org. Biomol. Chem.*, 7:739-746, 2009.

Rampalakos and Wulff, "A novel bis-thiourea organocatalyst for the asymmetric Aza-Henry reaction," *Advan. Synthesis Catalysis*, 350:1785-1790, 2008.

Saibabu Kotti et al., "Vicinal diamino functionalities as privileged structural elements in biologically active compounds and exploitation of their synthetic chemistry," *Chem. Biol. Drug Des.*, 67:101-114, 2006.

Satoh et al., "Reduction of organic compounds with sodium borohydride-transition metal salt systems : Reduction of organic nitrile, nitro and amide compounds to primary amines," *Tetrahedron Lett.*, 10:4555-4558, 1969.

Shen and Johnston, "A formal enantioselective acetate Mannich reaction: the nitro functional group as a traceless agent for activation and enantiocontrol in the synthesis of beta-amino acids," *Org. Lett.*, 10:4397-4400, 2008.

Ting and Schaus, "Organocatalytic asymmetric mannich reactions: new methodology, catalyst design, and synthetic applications," *Eur. J. Org. Chem.*, 35:5797-5815, 2007.

Vassilev et al., "In vivo activation of the p53 pathway by small-molecule antagonists of MDM2," *Science*, 303:844-848, 2004.

Vassilev, "Small-molecule antagonists of p53-MDM2 binding: research tools and potential therapeutics," *Cell Cycle*, 3:419-421, 2004.

Vögtle and Goldschmitt, "Die Diaza-Cope-Umlagerung," *Chemische Berichte*, 109:1-40, 1976. (English abstract).

Wagaw et al., "Palladium-Catalyzed Coupling of Optically Active Amines with Aryl Bromides," *J Am. Chem. Soc.*, 119:8451-8, 1997.

Wang et al., "Exploration of liquid and supercritical fluid chromatographic chiral separation and purification of Nutlin-3—a small molecule antagonist of MDM2," *J. Pharm. Biomed. Anal.*, 45:720-729, 2007.

Westermann, "Asymmetric Catalytic Aza-Henry Reactions Leading to 1,2-Diamines and 1,2-Diaminocarboxylic Acids," *Angew. Chem. Int. Ed.*, 42:151-153, 2003.

Xu et al., "Bifunctional-thiourea-catalyzed diastereo- and enantioselective aza-Henry reaction," *Chemistry*, 12:466-476, 2006.

Yamada et al., "The first catalytic asymmetric nitro-mannich-type reaction promoted by a new heterobimetallic complex," *Angew. Chem. Int. Ed.*, 38:3504-3506, 1999.

You and Kelly, "Highly efficient enantiospecific synthesis of imidazoline-containing amino acids using bis(triphenyl)oxodiphosphonium trifluoromethanesulfonate," *Org. Lett.*, 6:1681-1683, 2004.

You et al., "A biomimetic synthesis of thiazolines using hexaphenyloxodiphosphonium trifluoromethanesulfonate," *Angewandte Chemie. Intl. Ed.*, 42:83-85, 2003.

* cited by examiner

STEREOSELECTIVE METHODS, CATALYSTS AND INTERMEDIATES FOR THE SYNTHESIS OF (−)-NUTLIN-3 AND RELATED COMPOUNDS

The present application claims priority to U.S. Provisional Application Ser. No. 61/365,124, filed Jul. 16, 2010, the entire content of which is incorporated herein by reference in its entirety.

This invention was made with government support under grant GM 084333 from the National Institute of Health. The government has certain rights in the invention.

BACKGROUND OF THE INVENTION

I. Field of the Invention

The present invention relates generally to the field of chemistry. More particularly, it relates to synthetic methods, intermediates and catalysts for the synthesis of pharmaceuticals, including (−)-Nutlin-3.

II. Description of Related Art

Small molecules are attractive tools for drug development due to the ease with which they can be diversified structurally and functionally to optimize for potency, selectivity, and therapeutic window, while offering the long term possibility for large-scale production at relatively low cost. Chiral small molecules often provide versatility beyond achiral variants when attempting to disrupt the interaction between a peptide and its chiral receptor protein, but the additional stereochemical complexity can render a preparation long and cumbersome, or dependent on chromatographic techniques. A current case where a mismatch exists between therapeutic value and synthetic access is Nutlin-3, a chiral imidazoline discovered by Hoffmann-La Roche that inhibits p53-MDM2. Dubbed the 'Nutlins' as a general class of cis-4,5-disubstituted imidazolines, these small molecules have been in development as chemotherapeutics, and have emerged as powerful tools for the interrogation of a wide range of cellular signaling pathways. Although (−)-Nutlin-3 is >150 times more potent than its enantiomer ((+)-Nutlin-3), Nutlin-3 and its derivatives are still produced as the racemate, subjected to preparatory chiral chromatography, and the less active enantiomer—50% of the material synthesized—is discarded.

Inhibition of the oncoprotein MDM2 by a small molecule was validated as a strategy in 2004 when Vassilev and coworkers at Hoffmann-La Roche (HLR) reported that a class of chiral cis-4,5-disubstituted imidazolines (e.g., 1, dubbed the 'Nutlins') inhibit p53/MDM2 binding in vitro (Vassilev et al., 2004; Vassilev, 2004; Carvajal et al., 2005; Fry et al., 2005a; Fry et al., 2005b).

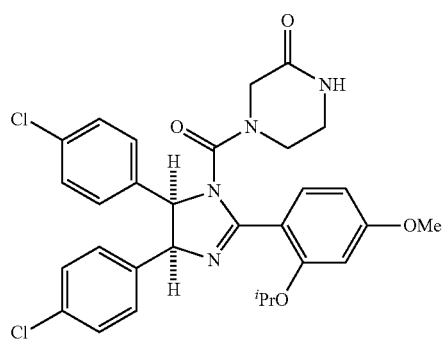

Nutlin-3 (1)

The p53 tumor suppressor network is autoregulated by MDM2, and for the approximate 50% of human cancers in which the p53 gene is wild-type, restoration of p53 and its associated network provides the cell with a pathway to apoptosis (Harris, 2006; Fischer and Lane, 2004; Bond et al., 2005). Furthermore, MDM2 is related to cell proliferation and survival through a range of interactions with additional proteins (Lowe et al., 2004). A rough estimate of the impact of the Nutlins might be assessed by noting that over 800 publications have cited the 2004 HLR paper in the intervening six years. In addition to their potential as biochemical probes and chemotherapeutics, the Nutlins provided a novel chemical scaffold from which to design small molecules that might rationally mimic the helical backbone of a peptide (Vassilev et al., 2004). This hypothesis was supported by X-ray crystallography of an MDM2-Nutlin complex in which the imidazoline occupied the native p53 ligand binding site.

As a chemotherapeutic, Nutlin-3 ultimately became the lead drug candidate, and 'enantiomer-a' binding was measured at 90 nM, about 151 times greater than its antipode 'enantiomer-b' (Vassilev et al., 2004). Despite the excitement surrounding the study of these small molecules as probes of cellular biology, supply issues for this chemotherapeutic currently limit its use on a larger scale, and the broader evaluation of the chemical biology of chiral nonracemic cis-imidazolines. Nutlin preparative details have been restricted to a series of patent disclosures to-date, and the absolute configuration of 'enantiomer-a' was suggested in a recent patent (U.S. Publn. 2005/282803). (−)-Nutlin-3 is available commercially from Cayman Chemical for approximately $85/mg. As the Nutlins migrate forward from their current preclinical position, the quantity of material needed for each phase will increase substantially.

One of the currently favored synthetic approach to the Nutlins (FIG. 1) illustrates how the underlying symmetry of the target was leveraged to prepare symmetrical (as amidine tautomers) imidazoline 6 in a concise manner (PCT Appln. WO 03/051359). The key cis-diamine 5 was prepared using a diaza-Cope reaction (Kim et al., 2008) from cis-diamine 4 (Vögtle and Goldschmitt, 1976). Although Nutlin-3 (1) is obtained after a single further transformation, it is formed as a racemate that requires a subsequent resolution. While this was possible for Nutlin-3 using expensive preparatory supercritical fluid chromatography equipped with a chiral stationary phase (Wang et al., 2007). In addition to the financial drawback associated with the separation, (+)-Nutlin-3 is a significantly weaker inhibitor of p53-MDM2, rendering this synthesis approach rather wasteful since the coproduction of the less potent enantiomer doubles the quantity of material at every step of the synthesis. Furthermore, a stoichiometric amount of cis-diamine 4 is required to prepare cis-diamine 5, and the use of a diaza-Cope reaction in this manner can efficiently furnish only symmetrical progeny. Therefore more practical methods for the synthesis of (−)-Nutlin-3 would be a great advantage.

SUMMARY OF THE INVENTION

In one aspect, the present disclosure provides methods for the preparation of a compound of Formula III comprising reacting a compound of Formula I:

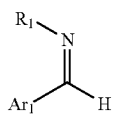
(I)

with a compound of Formula II:

(II)

in the presence of a catalyst to make a compound of Formula III:

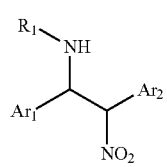
(III)

wherein:

Ar$_1$ and Ar$_2$ are each independently aryl$_{(C \leq 20)}$, substituted aryl$_{(C \leq 20)}$, heteroaryl$_{(C \leq 20)}$ or substituted heteroaryl$_{(C \leq 20)}$; and R$_1$ is hydrogen, trimethylsilyl or an amino-protecting group.

In some embodiments, the catalyst has Brønsted acidic and/or Brønsted basic properties. In some embodiments, the catalyst is a bis(amidine). In some embodiments, the reacting also occurs in the presence of co-catalyst. In some embodiments, the co-catalyst is an achiral Brønsted acid. In some embodiments, the Brønsted acid is triflic acid.

In some embodiments, the ratio of bis(amidine) to co-catalyst is about 1:1. In some embodiments, the bis(amidine) is chiral. In some embodiments, the bis(amidine) is C2-symmetric. In some embodiments, the bis(amidine) is further defined as:

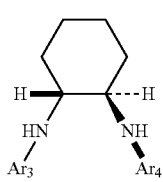

wherein Ar$_3$ and Ar$_4$ are each independently heteroaryl$_{(C \leq 20)}$ or substituted heteroaryl$_{(C \leq 20)}$, provide that both Ar$_3$ and Ar$_4$ each comprise at least one nitrogen atom.

In some embodiments, the bis(amidine) is:

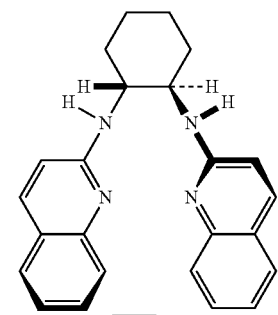

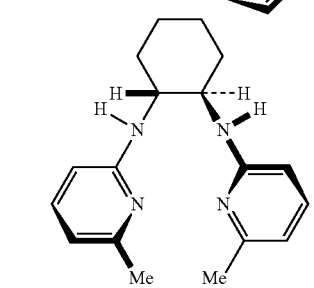

In some embodiments, the bis(amidine) is:

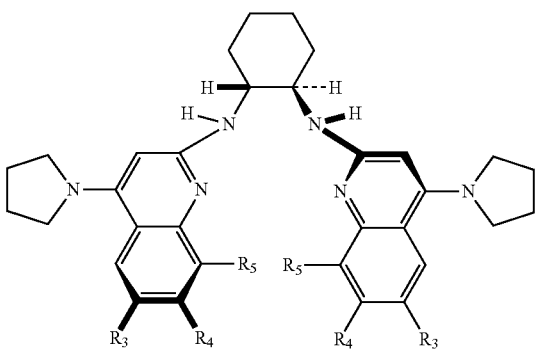

wherein R$_3$, R$_4$ and R$_5$ are each independently:
hydrogen, hydroxy, halo, amino, nitro, or cyano or thio; or
alkyl$_{(C \leq 6)}$, acyl$_{(C \leq 6)}$, alkoxy$_{(C \leq 6)}$, acyloxy$_{(C \leq 6)}$, alkylamino$_{(C \leq 6)}$, dialkylamino$_{(C \leq 6)}$, amido$_{(C \leq 6)}$, or a substituted version of any of these groups.

In some embodiments, R$_3$, R$_4$ or R$_5$ is hydrogen. In some embodiments, R$_3$, R$_4$ or R$_5$ is methoxy. In some embodiments, R$_3$, R$_4$ and R$_5$ is hydrogen. In some embodiments, R$_3$ is methoxy and both R$_4$ and R$_5$ are hydrogen. In some embodiments, R$_4$ is methoxy and both R$_3$ and R$_5$ are hydrogen. In some embodiments, both $R_3$ and $R_4$ are methoxy and $R_5$ is hydrogen. In some embodiments, both $R_3$ and $R_4$ are hydrogen and $R_5$ is methoxy.

In some embodiments, $R_1$ is an amino-protecting group. In some embodiments, the method further comprises removing the amino-protecting group. In some embodiments, the amino-protecting group is Boc, Fmoc, Cbz, acetyl, trifluoroacetyl, benzyl, triphenylmethyl or p-toluenesulfonyl. In some embodiments, the amino-protecting group is Boc.

In some embodiments, $Ar_1$ is aryl$_{(C \leq 18)}$ or substituted aryl$_{(C \leq 18)}$. In some embodiments, $Ar_1$ is substituted aryl$_{(C \leq 18)}$. In some embodiments, $Ar_2$ is aryl$_{(C \leq 18)}$ or substituted aryl$_{(C \leq 18)}$. In some embodiments, $Ar_2$ is substituted aryl$_{(C \leq 18)}$. In some embodiments, $Ar_1$ and $Ar_2$ are the same. In some embodiments, both $Ar_1$ and $Ar_2$ are p-chlorophenyl. In some embodiments, $Ar_1$ and $Ar_2$ are different.

In some embodiments, the method further comprises admixing the compounds of formulas I and II in a solvent to make a solution. In some embodiments, the compounds of formulas I and II are soluble in the solvent. In some embodiments, the solvent is toluene. In some embodiments, the method further comprises cooling the solution to below −20° C. In some embodiments, the method further comprises admixing the catalyst with the solvent.

In some embodiments, the ratio of catalyst to compound of formula I is 0.1 mol % to 25 mol %. In some embodiments, the ratio is 0.1 mol % to 5 mol %. In some embodiments, one optical isomer of the compound of formula III is made with a diastereomeric ratio (dr) greater than 10:1 and an enantiomer excess (ee) greater than 85%.

In some embodiments, the optical isomer has the formula IIIa:

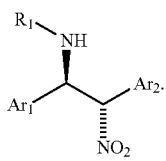

(IIIa)

wherein:
  $Ar_1$ and $Ar_2$ are each independently aryl$_{(C \leq 20)}$, substituted aryl$_{(C \leq 20)}$, heteroaryl$_{(C \leq 20)}$ or substituted heteroaryl$_{(C \leq 20)}$; and
  $R_1$ is an amino-protecting group.

In some embodiments, the dr is from about 12:1 to about 100:1. In some embodiments, the ee is from about from about 90% to about 99%.

In another aspect of the present disclosure, there is provided a method for the preparation of (−)-Nutlin-3 comprising:

(a) reacting

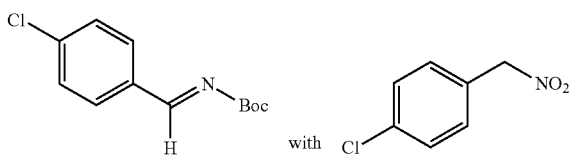 [SMILES: CC(C)(C)OC(=O)/N=C/c1ccc(Cl)cc1 ; O=[N+]([O-])Cc1ccc(Cl)cc1]

in the presence of a catalyst to make

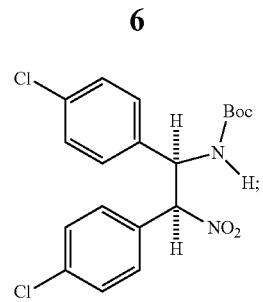

(b) reacting

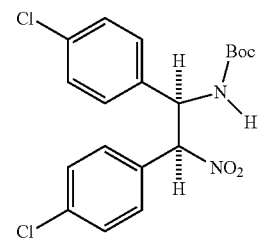 [SMILES: CC(C)(C)OC(=O)N[C@H](c1ccc(Cl)cc1)[C@H](c1ccc(Cl)cc1)[N+](=O)[O-]]

with a reducing agent to make

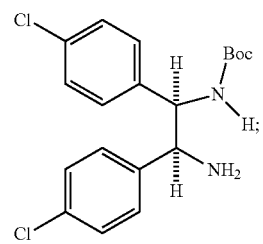

(c) acylating

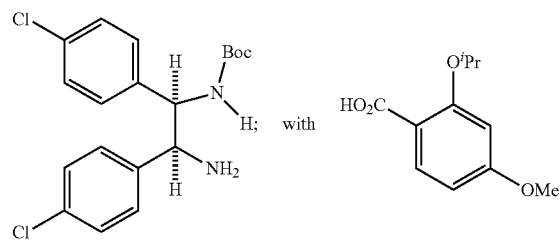

to make

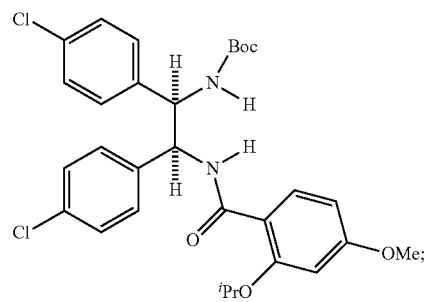 [SMILES: COc1ccc(C(=O)N[C@@H](c2ccc(Cl)cc2)[C@H](NC(=O)OC(C)(C)C)c2ccc(Cl)cc2)c(OC(C)C)c1]

(d) deprotecting

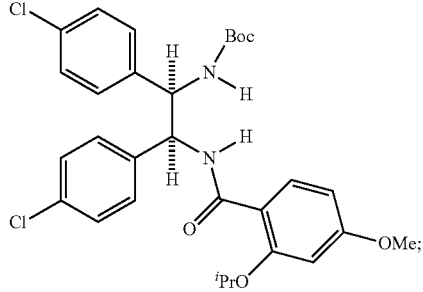 [SMILES: COc1ccc(C(=O)N[C@@H](c2ccc(Cl)cc2)[C@H](NC(=O)OC(C)(C)C)c2ccc(Cl)cc2)c(OC(C)C)c1]

with a deprotecting acid or thermally to make

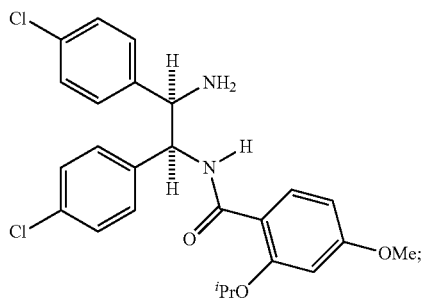 [SMILES: COc1ccc(C(=O)N[C@@H](c2ccc(Cl)cc2)[C@H](N)c2ccc(Cl)cc2)c(OC(C)C)c1]

(e) reacting

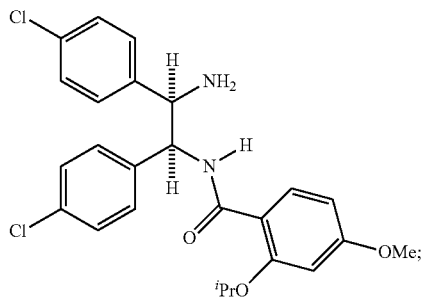 [SMILES: COc1ccc(C(=O)N[C@@H](c2ccc(Cl)cc2)[C@H](N)c2ccc(Cl)cc2)c(OC(C)C)c1]

with carbonyl diimidazole (CDI) in the presence of piperazinone to make

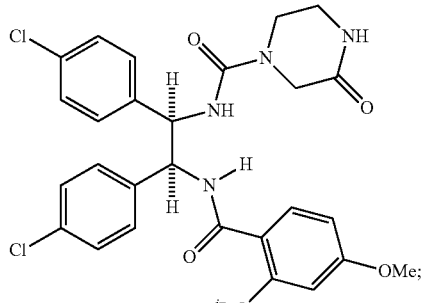

and (f) reacting

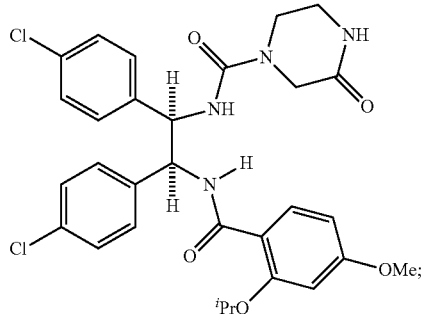 [SMILES: COc1ccc(C(=O)N[C@@H](c2ccc(Cl)cc2)[C@H](NC(=O)N2CCNC(=O)C2)c2ccc(Cl)cc2)c(OC(C)C)c1]

with a dehydrating agent to make (−)-Nutlin-3.

In some embodiments, the catalyst comprises a bis(amidine). In some embodiments, the catalyst further comprises a Brønsted acid. In some embodiments, the Brønsted acid is triflic acid. In some embodiments, the catalyst comprises about equivalent molar quantities of the bis(amidine) and the Brønsted acid. In some embodiments, the bis(amidine) is chiral. In some embodiments, the bis(amidine) is $C_2$-symmetric.

In some embodiments, the bis(amidine) is further defined as:

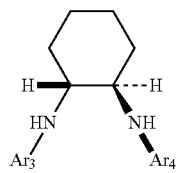

wherein $Ar_3$ and $Ar_4$ are each independently heteroaryl$_{(C \leq 20)}$ or substituted heteroaryl$_{(C \leq 20)}$, provide that both $Ar_3$ and $Ar_4$ each comprise a nitrogen atom connected with no intervening atoms to the atom at the group's point of attachment.

In some embodiments, the bis(amidine) is:

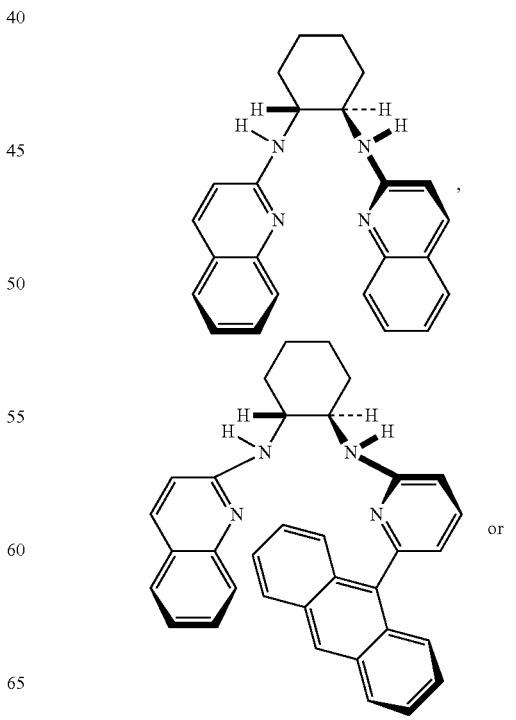

or

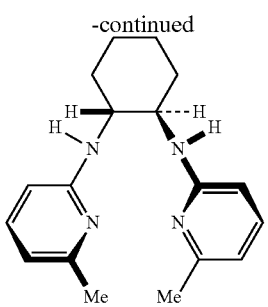

In some embodiments, the bis(amidine) is:

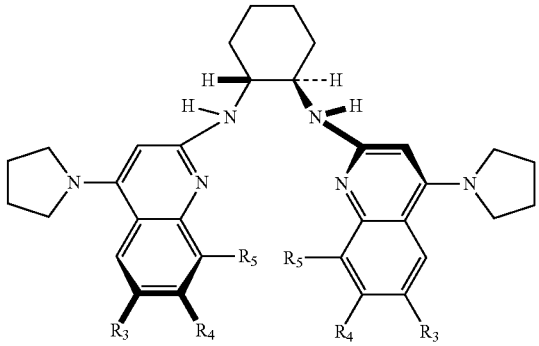

wherein $R_3$, $R_4$ and $R_5$ are each independently:
hydrogen, hydroxy, halo, amino, nitro, or cyano or thio; or alkyl$_{(C\leq6)}$, acyl$_{(C\leq6)}$, alkoxy$_{(C\leq6)}$, acyloxy$_{(C\leq6)}$, alkylamino$_{(C\leq6)}$, dialkylamino$_{(C\leq6)}$, amido$_{(C\leq6)}$, or a substituted version of any of these groups.

In some embodiments, $R_3$, $R_4$ or $R_5$ is hydrogen. In some embodiments, $R_3$, $R_4$ or $R_5$ is methoxy. In some embodiments, $R_3$, $R_4$ and $R_5$ is hydrogen. In some embodiments, $R_3$ is methoxy and both $R_4$ and $R_5$ are hydrogen. In some embodiments, $R_4$ is methoxy and both $R_3$ and $R_5$ are hydrogen. In some embodiments, both $R_3$ and $R_4$ are methoxy and $R_5$ is hydrogen. In some embodiments, both $R_3$ and $R_4$ are hydrogen and $R_5$ is methoxy.

In some embodiments, the reducing agent comprises NaBH$_4$ and a transition metal salt. In some embodiments, the transition metal salt is CoCl$_2$. In some embodiments, the reducing agent comprises hydrogen and a hydrogenation catalyst. In some embodiments, the reducing agent is Zn and an acid. In some embodiments, the acid is HCl. In some embodiments, the deprotecting acid is trifluoroacetic acid.

In some embodiments, the dehydrating agent comprises triphenylphosphine oxide. In some embodiments, the dehydrating agent further comprises triflic anhydride.

In another aspect of the present disclosure there is provide a method for the preparation of (−)-Nutlin-3 comprising reacting

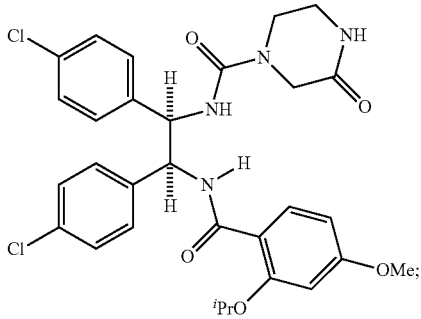 [SMILES: COc1ccc(C(=O)N[C@@H](c2ccc(Cl)cc2)[C@H](NC(=O)N2CCNC(=O)C2)c2ccc(Cl)cc2)c(OC(C)C)c1]

with a dehydrating agent to make (−)-Nutlin-3.

In some embodiments, the dehydrating agent comprises triphenylphosphine oxide.

In some embodiments, the dehydrating agent further comprises triflic anhydride.

In another aspect of the present disclosure there are provided compounds of the formula:

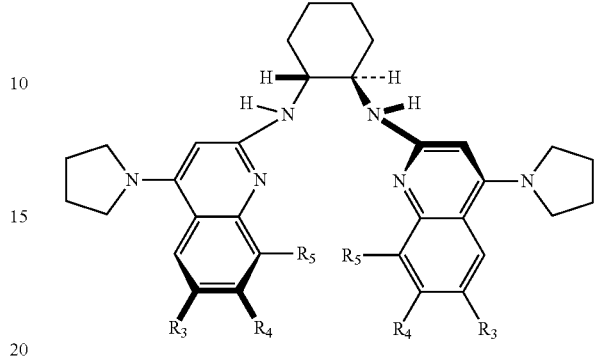

wherein $R_3$, $R_4$ and $R_5$ are each independently:
hydrogen, hydroxy, halo, amino, nitro, or cyano or thio; or alkyl$_{(C\leq6)}$, acyl$_{(C\leq6)}$, alkoxy$_{(C\leq6)}$, acyloxy$_{(C\leq6)}$, alkylamino$_{(C\leq6)}$, dialkylamino$_{(C\leq6)}$, amido$_{(C\leq6)}$, or a substituted version of any of these groups;
provided that at least one of $R_3$, $R_4$ and $R_5$ is not hydrogen.

In some embodiments, $R_3$, $R_4$ or $R_5$ is methoxy. In some embodiments, $R_3$ is methoxy and both $R_4$ and $R_5$ are hydrogen. In some embodiments, $R_4$ is methoxy and both $R_3$ and $R_5$ are hydrogen. In some embodiments, both $R_3$ and $R_4$ are methoxy and $R_5$ is hydrogen. In some embodiments, both $R_3$ and $R_4$ are hydrogen and $R_5$ is methoxy.

In another aspect of the present disclosure there are provided compounds of the formula:

(III)

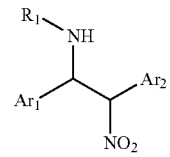

wherein:
Ar$_1$ and Ar$_2$ are each independently aryl$_{(C\leq20)}$, substituted aryl$_{(C\leq20)}$, heteroaryl$_{(C\leq20)}$ or substituted heteroaryl$_{(C\leq20)}$; and
$R_1$ is hydrogen, trimethylsilyl or an amino-protecting group.

In some embodiments, $R_1$ is an amino-protecting group. In other embodiments, $R_1$ is H. In some embodiments, the amino-protecting group is Boc, Fmoc, Cbz, acetyl, trifluoroacetyl, benzyl, triphenylmethyl or p-toluenesulfonyl. In some embodiments, the amino-protecting group is Boc. In some embodiments, Ar$_1$ is aryl$_{(C\leq18)}$ or substituted aryl$_{(C\leq18)}$. In some embodiments, Ar$_1$ is substituted aryl$_{(C\leq18)}$. In some embodiments, Ar$_2$ is aryl$_{(C\leq18)}$ or substituted aryl$_{(C\leq18)}$. In some embodiments, Ar$_2$ is substituted aryl$_{(C\leq18)}$. In some embodiments, Ar$_1$ and Ar$_2$ are the same. In some embodiments, both Ar$_1$ and Ar$_2$ are p-chlorophenyl. In some embodiments, Ar$_1$ and Ar$_2$ are different.

In some embodiments, a stereoisomer of formula III is present with a diastereomeric ratio (dr) from about 10:1 to about 100:1 and an enantiomer excess (ee) from about 85% to about 100%.

In some embodiments, the stereoisomer has the formula IIIa:

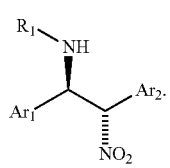

wherein:

Ar$_1$ and Ar$_2$ are each independently aryl$_{(C \leq 20)}$, substituted aryl$_{(C \leq 20)}$, heteroaryl$_{(C \leq 20)}$ or substituted heteroaryl$_{(C \leq 20)}$; and R$_1$ is an amino-protecting group.

In some embodiments, the dr is from about 12:1 to about 100:1. In some embodiments, the ee is from about from about 90% to about 99%.

Other objects, features and advantages of the present disclosure will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description. Note that simply because a particular compound is ascribed to one particular generic formula doesn't mean that it cannot also belong to another generic formula.

BRIEF DESCRIPTION OF THE DRAWINGS

The following drawings form part of the present specification and are included to further demonstrate certain aspects of the present disclosure. The invention may be better understood by reference to one of these drawings in combination with the detailed description of specific embodiments presented herein.

DESCRIPTION OF ILLUSTRATIVE EMBODIMENTS

In one aspect of the present disclosure, there are provided methods and intermediates for the preparation of (−)-Nutlin-3. In other aspects, there are provided methods and intermediates for the enantioselective addition of an aryl nitromethane to an aldimine. In other aspects, there are provided novel bis(amidine) compounds that may be used as catalysts in either of the above as well as in other methods. Additional details are provided below.

I. Enantioselective Synthesis of cis-Stilbene-Related Intermediates

In one aspect, the present disclosure provides a new methods for the addition of aryl nitromethanes (e.g., 8) to aryl N-Boc aldimines. In some embodiments, this additions is diastereo- and/or enantioselective. These methods may used to remove the current reliance on preparatory chromatography using a chiral stationary phase, substituting it, for example, with a readily prepared chiral catalyst that furnishes intermediate, e.g., 7 (FIG. 2) with high stereoselection. The ease of preparation of such intermediates is expected to increase the accessibility of cis-imidazolines to chemical biologists, thereby stimulating their broader use as probes if not providing the promise of their practical synthesis to fuel studies related to drug development.

Thus, in one aspect, the invention provides methods for the preparation of a compound of Formula III comprising, reacting a compound of Formula I:

with a compound of Formula II:

in the presence of a catalyst to make a compound of Formula III:

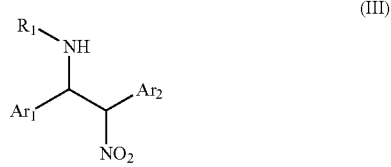

wherein:
Ar$_1$ and Ar$_2$ are each independently aryl$_{(C \leq 20)}$, substituted aryl$_{(C \leq 20)}$, heteroaryl$_{(C \leq 20)}$ or substituted heteroaryl$_{(C \leq 20)}$; and R$_1$ is hydrogen, trimethylsilyl or an amino-protecting group.

Further details regarding different embodiments are provided below and in the summary above. For example, in many such embodiments the coupling proceeds enantioselectively and/or diastereoselectively.

Figure 2:
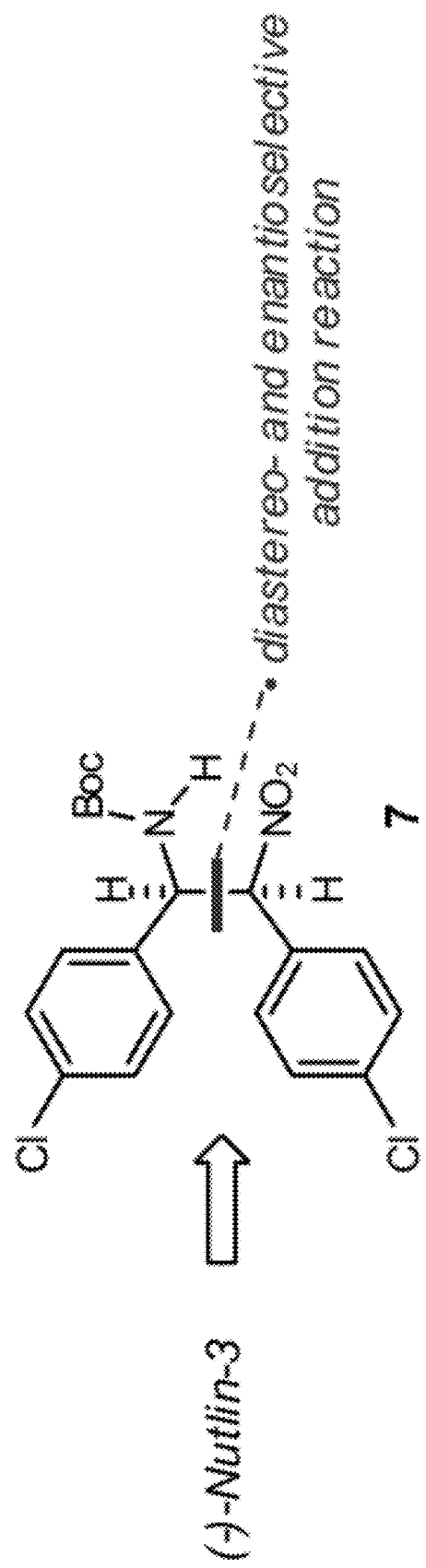
FIG. 2—Retrosynthetic Analysis for (−)-Nutlin-3. This scheme illustrates the need for a stereoselective synthesis of a functional equivalent to a cis-stilbene diamine.

In some embodiments, there is provided β-amino nitroalkane intermediate 7, as well as derivatives thereof. This intermediate may be prepared using an aza-Henry reaction and an aryl nitromethane pronucleophile (FIG. 2). For reviews of aza-Henry reactions, see Marques-Lopez et al., 2009; Akiyama et al., 2006; Ting and Schaus, 2007; Westermann, 2003; Adams et al., 1998; Yamada et al., 1999; Knudsen et al., 2001; Okino et al., 2004; Bernardi et al., 2005; Fini et al., 2005; Palomo et al., 2005; Xu et al., 2006; Rampalakos and Wulff, 2008, each of which are incorporated herein by reference.

Figure 7:
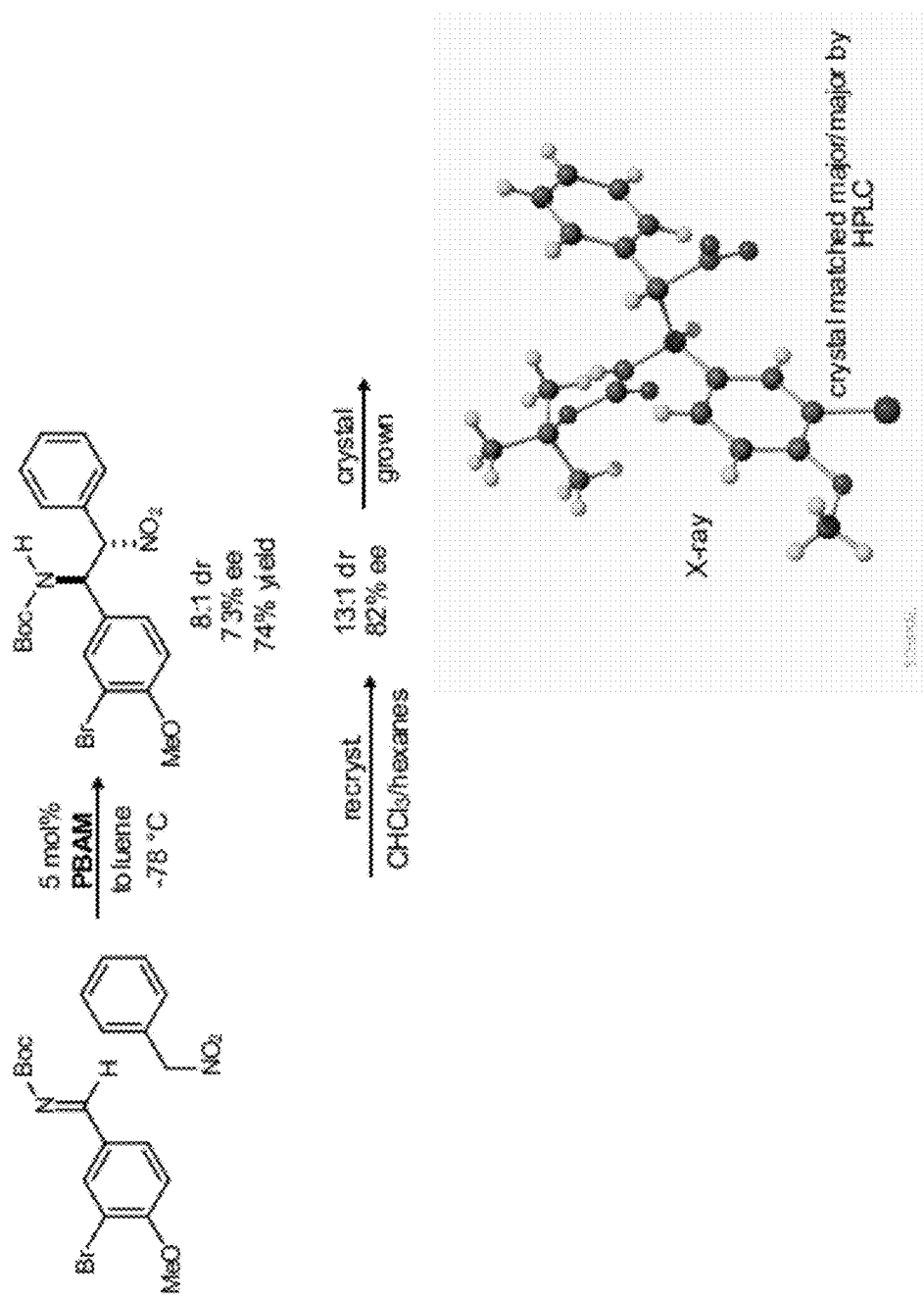
FIG. 7—Aza-Henry Coupling Using Reagents with Different Aryl Groups. Under the conditions summarized in the reaction scheme, the coupling reaction proceeds at 73% ee and 13:1 dr. Crystals of the coupling product were grown which provided the stereochemistry of the major/major isomer.
Figure 8:
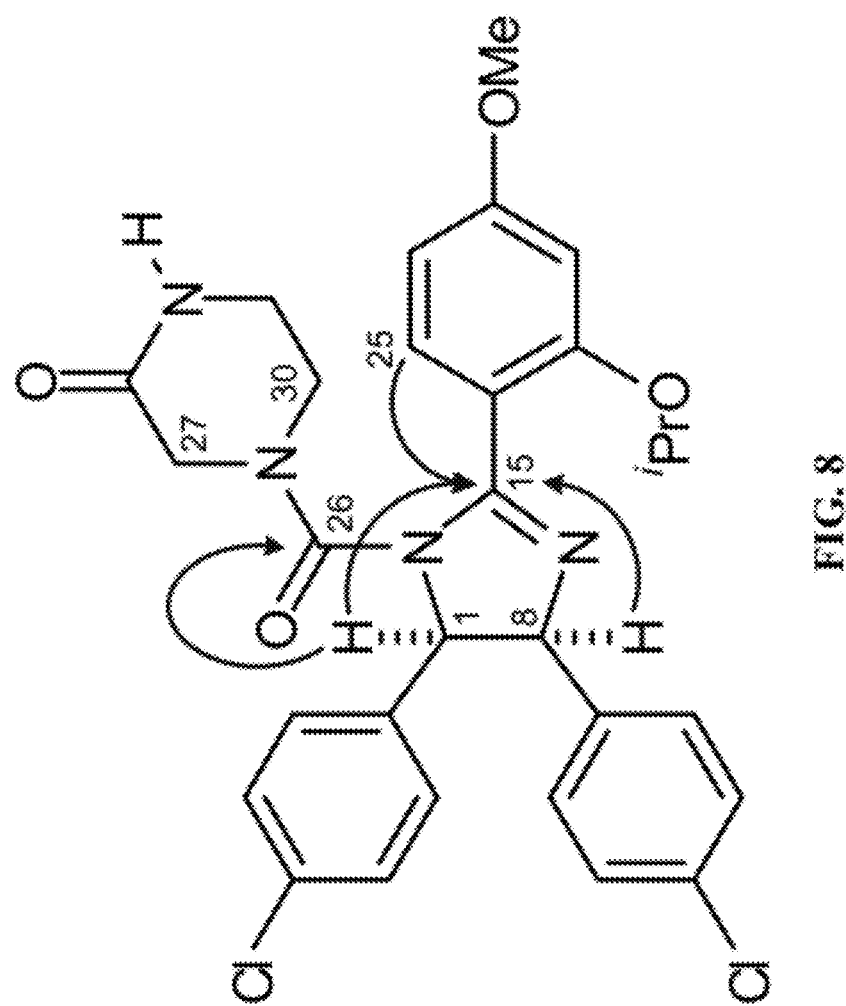
FIG. 8.—Nutlin-3 HMBC Correlations (600 MHz). Further evidence supporting the structural assignment includes this HMBC, which clearly showed the anticipated couplings for Nutlin-3. C26 (155 ppm) showed correlations to H27/H27' and H30/H30' and to H1 (but not H8). C15 (160 ppm) showed correlations to both of the imidazoline methines (H1 and H8) and also to the H25.

Example 1 provides the results of several experiments applying these principles to the coupling of 8 and 9 (FIG. 3) to make 7. FIG. 7 provides an example of an embodiment wherein two reagents having different aryl groups are coupled by the method disclosed herein. In this example, stereochemical configuration was obtained using X-ray crystallography.

These methods can be further modified and optimized using the principles and techniques of organic chemistry as applied by a person skilled in the art. Such principles and techniques are taught, for example, in March's Advanced Organic Chemistry: Reactions, Mechanisms, and Structure (2007), which is incorporated by reference herein.

II. Methods and Intermediates for the Synthesis of (−)-NUTLIN-3

Figure 1:
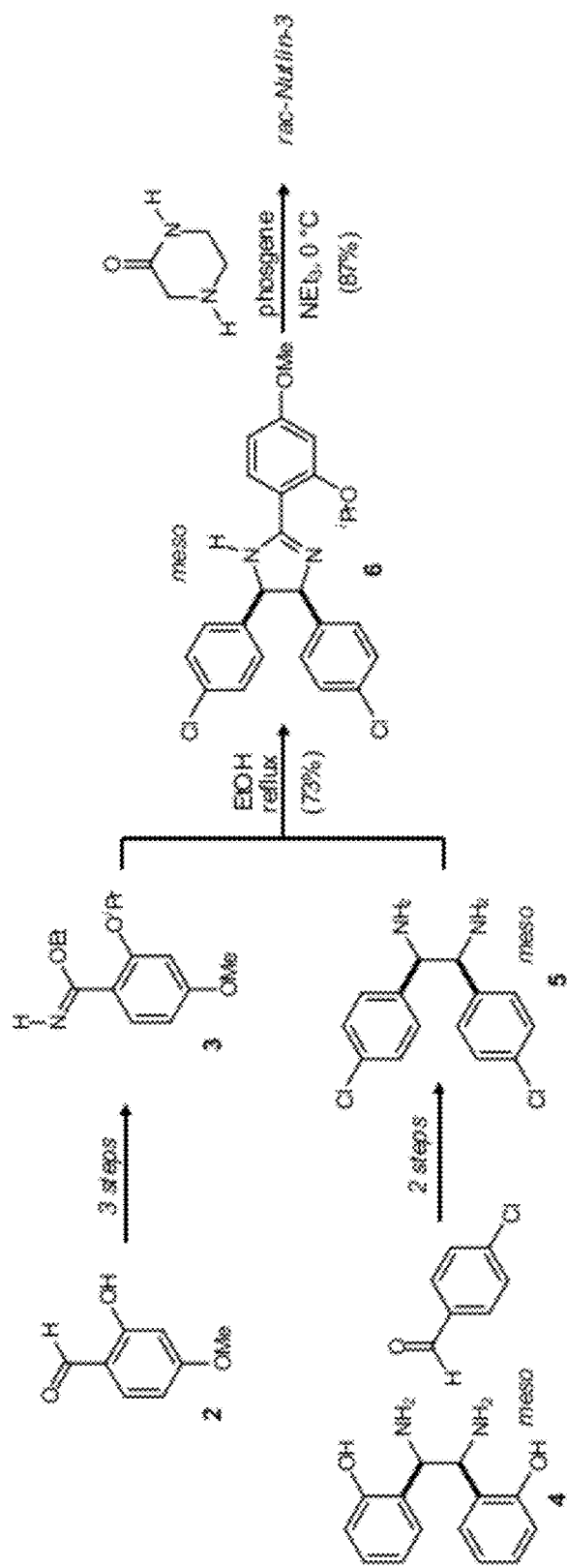
FIG. 1—A Currently Used Synthesis of Racemic Nutlin-3. Cis-diamine 5 was prepared using a diaza-Cope reaction from cis-diamine 4. From diamine 5, the symmetrical (as amidine tautomers) imidazoline 6 was prepared. Racemic Nutlin-3 is then obtained after a single further transformation.

In another aspect, there are provided improved methods for making (−)-Nutlin-3, including methods that avoid meso-intermediate 6 (FIG. 1) and its attendant limitations. In some embodiments, a synthetic equivalent to the underlying cis-stilbene diamine could be prepared enantioselectively and with a structural dissymmetry that could be preserved through the final step. For reviews describing vic-diamines and their preparation, see (Lucet et al., 1998; Faugeroux and Genisson, 2008; Kotti et al., 2006; Mortensen and O'Doherty, 2005), which are incorporated by reference herein. For metal-catalyzed diamination reactions, see (Cardona and Goti, 2009) which is incorporated by reference herein.

Figure 3:
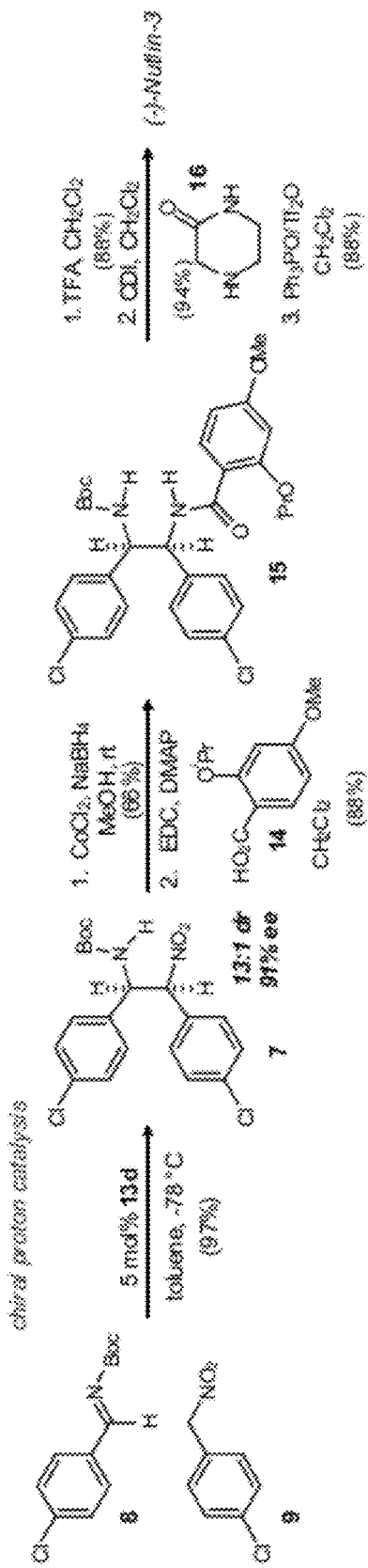
FIG. 3—Preparation of (−)-Nutlin-3. This synthetic scheme for this fully stereocontrolled synthesis is explained in Example 2.

In the embodiment of the scheme shown in FIG. 3, intermediate 7 was further reacted to reduce the nitro group to an amine using cobalt boride formed in situ (Satoh et al., 1969), and subsequent acylation with acid 14 to produce Boc-protected amide 15 (FIG. 3). Straightforward deprotection of the Boc group using trifluoroacetic acid revealed the secondary amine in 88% yield. Acylation of the amine with carbonyl diimidazole led to an intermediate isocyanate that was treated with piperazinone 16.

This set the stage to attempt a chemoselective cyclizative dehydration to the desired imidazoline. In other embodiments, this approach may also be used for the preparation of cis-imidazoline heterocycles bearing an underlying symmetrical cis-stilbene diamine backbone, as well as analogs derived from unsymmetrical cis-stilbene diamines.

Figure 4:
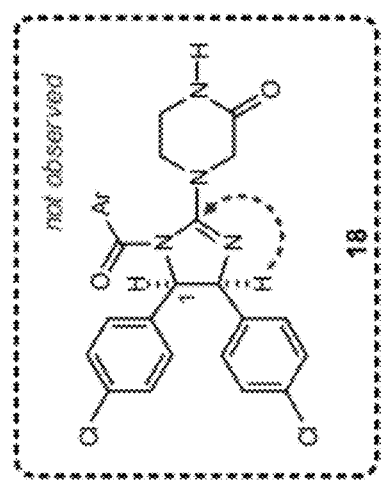
FIG. 4—Dehydrative Cyclization of 17. This figure illustrates HMBC correlations ($^3J_{HC}$) Consistent with Selective Production of Nutlin-3 (1) and not the alternative cyclization isomer (18).
Figure 4:
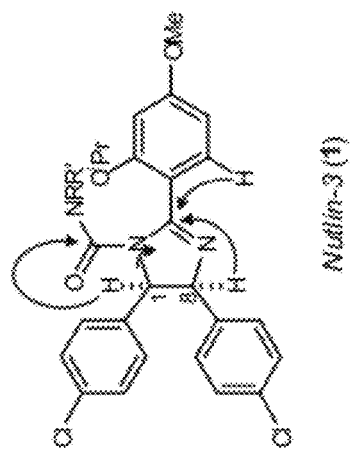
Figure 4:
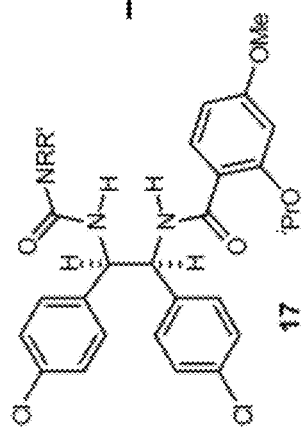

In the embodiment of the scheme shown in FIG. 4, dehydration was accomplished phosphonium anhydride formed by the combination of triphenyl phosphine oxide and triflic anhydride. This protocol was described by Hendrickson, who demonstrated its use in a variety of amide dehydrative cyclizations (Hendrickson and Schwartzman, 1975; Hendrickson and Hussoin, 1989; Hendrickson and Hussoin, 1987). Examples of heterocycle formation using this reagent has been described in several contexts. See (You and Kelly, 2004; You et al., 2003; Petersson et al., 2009; Petersson et al., 2008), which are incorporated herein by references. Faced with the context of mixed amide/carbamate 17 (FIG. 4), the Hendrickson protocol was applied and a single imidazoline product was observed that was retrieved in 88% isolated yield. Additional details are provided in Example 2 below. In this manner, an underlying cis-stilbene diamine backbone may thereby be further transformed to the cis-imidazoline heterocycle by a sequence that preserves the asymmetry without further use of protecting groups.

Figure 6:
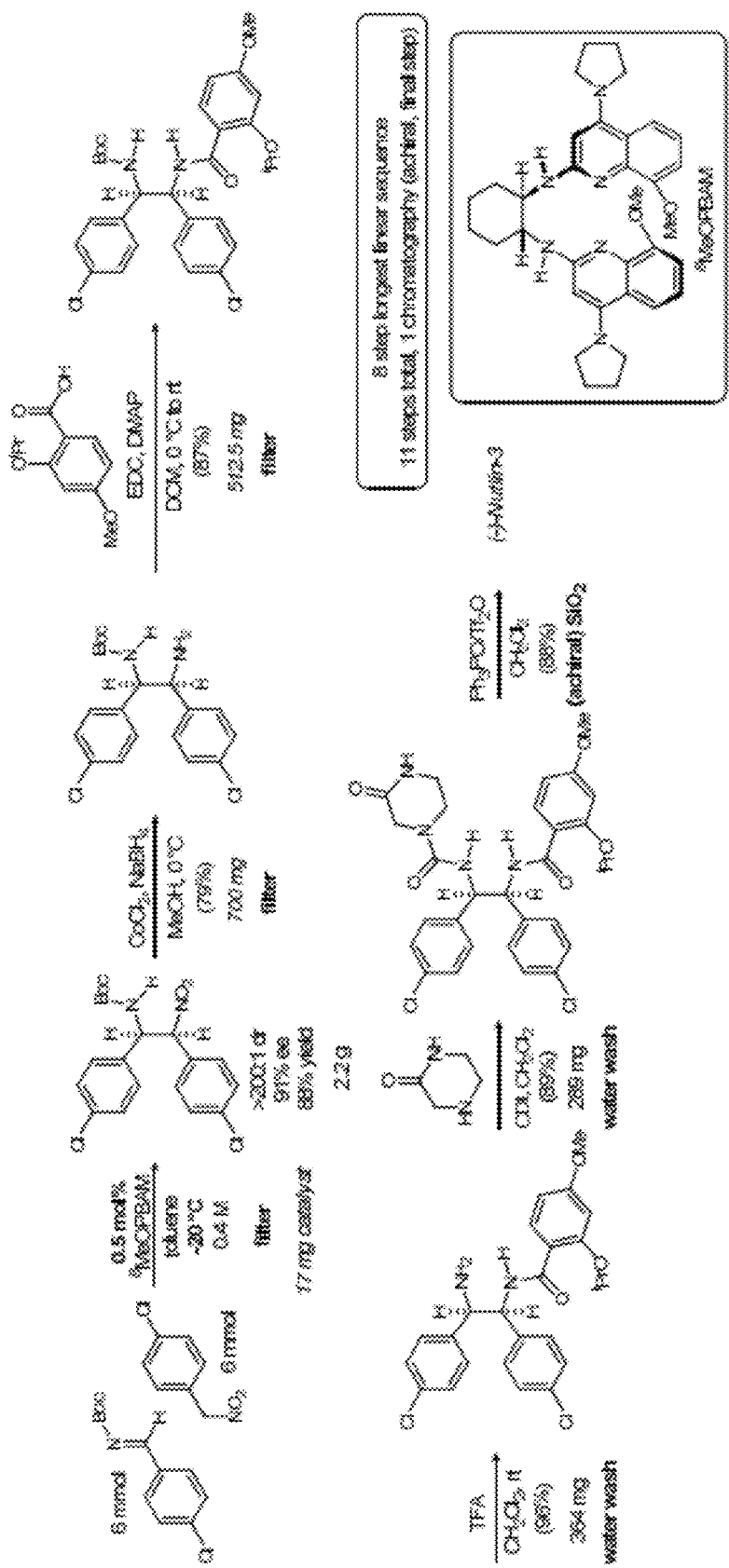
FIG. 6—Preparative Scale synthesis of (−)-Nutlin 3. This reaction scheme summarizes yields, conditions and the catalyst used for a stereocontrolled synthesis of (−)-Nutlin 3.
Figure 9:
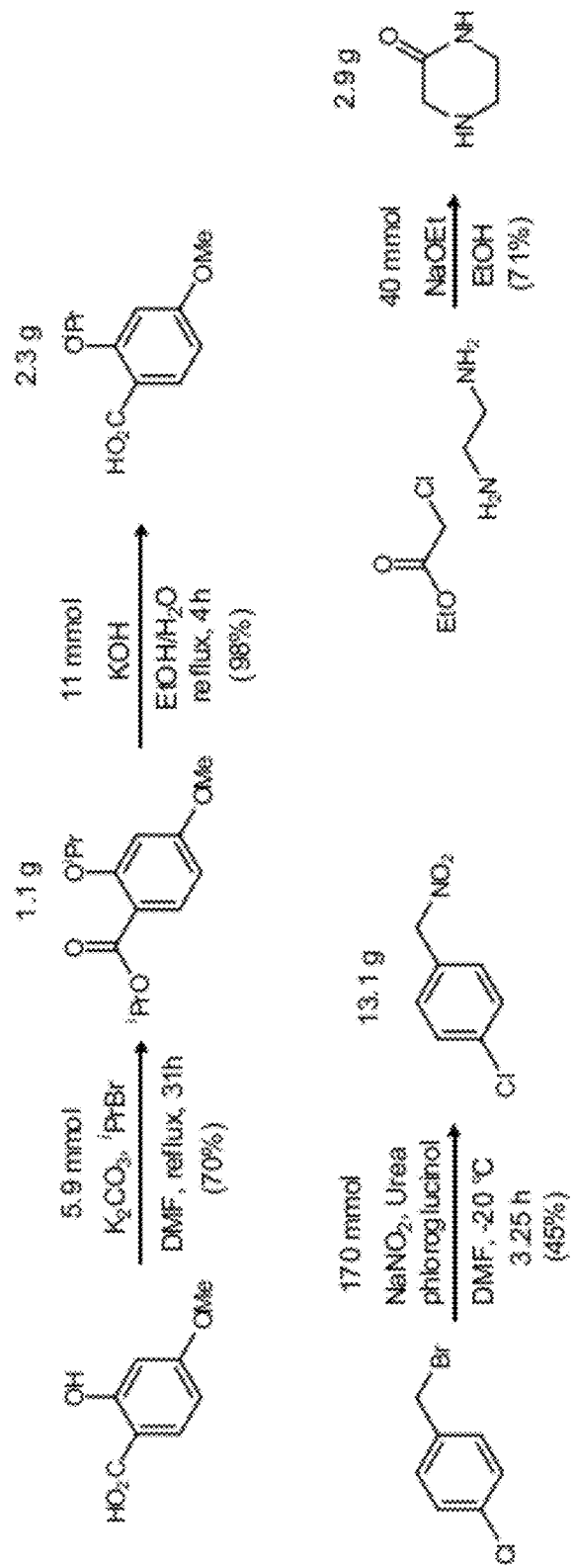
FIGS. 9 & 10—Preparative Scale synthesis of (−)-Nutlin 3. These reaction schemes summarize yields, conditions and the catalyst used for a stereocontrolled synthesis of (−)-Nutlin 3.
Figure 10:
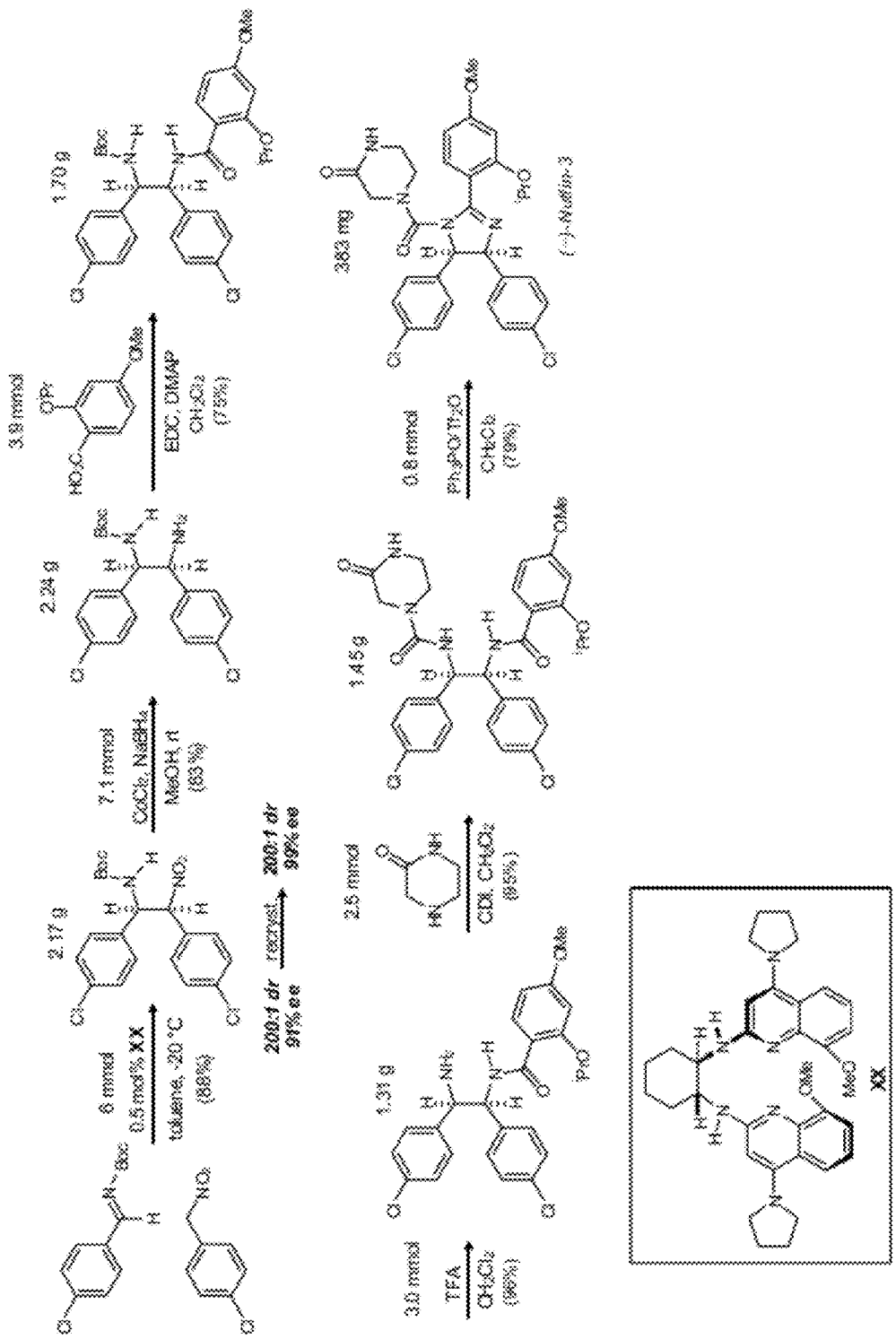

In other embodiments, (−)-Nutlin-3 may be made according to the synthetic schemes shown in FIGS. 6, 9 and 10.

These methods can be further modified and optimized using the principles and techniques of organic chemistry as applied by a person skilled in the art. Such principles and techniques are taught, for example, in March's Advanced Organic Chemistry: Reactions, Mechanisms, and Structure (2007), which is incorporated by reference herein.

III. Novel Bis(Amidine) Catalysts

Also provided herein are novel bis(amidine) catalysts of the formula:

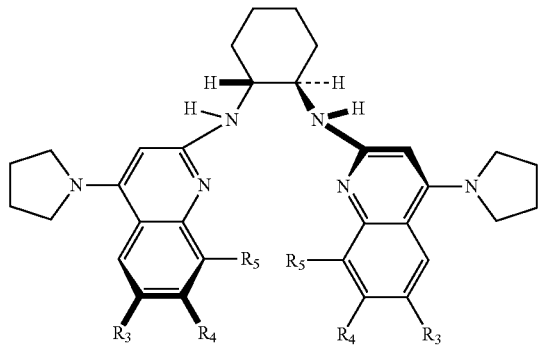

wherein R$_3$, R$_4$ and R$_5$ are each independently:
hydrogen, hydroxy, halo, amino, nitro, or cyano or thio; or
alkyl$_{(C \leq 6)}$, acyl$_{(C \leq 6)}$, alkoxy$_{(C \leq 6)}$, acyloxy$_{(C \leq 6)}$, alkylamino$_{(C \leq 6)}$, dialkylamino$_{(C \leq 6)}$, amido$_{(C \leq 6)}$, or a substituted version of any of these groups;
provided that at least one of R$_3$, R$_4$ and R$_5$ is not hydrogen.

In some embodiments, R$_3$, R$_4$ or R$_5$ is methoxy. In some embodiments, R$_3$ is methoxy and both R$_4$ and R$_5$ are hydrogen. In some embodiments, R$_4$ is methoxy and both R$_3$ and R$_5$ are hydrogen. In some embodiments, both R$_3$ and R$_4$ are methoxy and R$_5$ is hydrogen. In some embodiments, both R$_3$ and R$_4$ are hydrogen and R$_5$ is methoxy.

These catalysts may be used to facilitate the synthesis of important chemical and pharmaceutical intermediates, including intermediate 7, as shown in Example 1 below.

These bis(amidine) catalysis may be made using the methods outlined in the Examples section. These methods can be further modified and optimized using the principles and techniques of organic chemistry as applied by a person skilled in the art. Such principles and techniques are taught, for example, in March's Advanced Organic Chemistry: Reactions, Mechanisms, and Structure (2007), which is incorporated by reference herein.

IV. Process Scale-up

The above methods can be further modified and optimized for preparative, pilot- or large-scale production, either batch of continuous, using the principles and techniques of process chemistry as applied by a person skilled in the art. Such principles and techniques are taught, for example, in Practical Process Research & Development (2000), which is incorporated by reference herein. For example, the scheme and results summarized Example 4 and in FIGS. 6, 9 and 10 show preparative scale syntheses of (−)-Nutlin 3.

V. Definitions

When used in the context of a chemical group, "hydrogen" means —H; "hydroxy" means —OH; "oxo" means =O; "halo" means independently —F, —Cl, —Br or —I; "amino" means —$NH_2$ (see below for definitions of groups containing the term amino, e.g., alkylamino); "hydroxyamino" means —NHOH; "nitro" means —$NO_2$; imino means =NH (see below for definitions of groups containing the term imino, e.g., alkylimino); "cyano" means —CN; "azido" means —$N_3$; in a monovalent context "phosphate" means —OP(O)$(OH)_2$ or a deprotonated form thereof; in a divalent context "phosphate" means —OP(O)(OH)O— or a deprotonated form thereof; "mercapto" means —SH; "thio" means =S; "thioether" means —S—; "sulfonamido" means —NHS$(O)_2$— (see below for definitions of groups containing the term sulfonamido, e.g., alkylsulfonamido); "sulfonyl" means —$S(O)_2$— (see below for definitions of groups containing the term sulfonyl, e.g., alkylsulfonyl); "sulfinyl" means —S(O)— (see below for definitions of groups containing the term sulfinyl, e.g., alkylsulfinyl); and "silyl" means —$SiH_3$ (see below for definitions of group(s) containing the term silyl, e.g., alkylsilyl).

The symbol "—" means a single bond, "=" means a double bond, and "≡" means triple bond. The symbol "====" represents a single bond or a double bond. The symbol "⌇", when drawn perpendicularly across a bond indicates a point of attachment of the group. It is noted that the point of attachment is typically only identified in this manner for larger groups in order to assist the reader in rapidly and unambiguously identifying a point of attachment. The symbol "◂▬" means a single bond where the group attached to the thick end of the wedge is "out of the page." The symbol "▬▮▮▮" means a single bond where the group attached to the thick end of the wedge is "into the page". The symbol "⌇" means a single bond where the conformation is unknown (e.g., either R or S), the geometry is unknown (e.g., either E or Z) or the compound is present as mixture of conformation or geometries (e.g., a 50%/50% mixture).

For the groups below, the following parenthetical subscripts further define the groups as follows: "(Cn)" defines the exact number (n) of carbon atoms in the group. "(C≤n)" defines the maximum number (n) of carbon atoms that can be in the group, with the minimum number of carbon atoms in such at least one, but otherwise as small as possible for the group in question, e.g., it is understood that the minimum number of carbon atoms in the group "alkyl$_{(C≤8)}$" is two. For example, "alkoxy$_{(C≤10)}$" designates those alkoxy groups having from 1 to 10 carbon atoms (e.g., 1, 2, 3, 4, 5, 6, 7, 8, 9, or 10, or any range derivable therein (e.g., 3 to 10 carbon atoms). (Cn-n') defines both the minimum (n) and maximum number (n') of carbon atoms in the group. Similarly, "alkyl$_{(C2-10)}$" designates those alkyl groups having from 2 to 10 carbon atoms (e.g., 2, 3, 4, 5, 6, 7, 8, 9, or 10, or any range derivable therein (e.g., 3 to 10 carbon atoms)).

The term "alkyl" when used without the "substituted" modifier refers to a non-aromatic monovalent group with a saturated carbon atom as the point of attachment, a linear or branched, cyclo, cyclic or acyclic structure, no carbon-carbon double or triple bonds, and no atoms other than carbon and hydrogen. The groups, —$CH_3$ (Me), —$CH_2CH_3$ (Et), —$CH_2CH_2CH_3$ (n-Pr), —$CH(CH_3)_2$ (iso-Pr), —$CH(CH_2)_2$ (cyclopropyl), —$CH_2CH_2CH_2CH_3$ (n-Bu), —$CH(CH_3)$ $CH_2CH_3$ (sec-butyl), —$CH_2CH(CH_3)_2$ (iso-butyl), —$C(CH_3)_3$ (tert-butyl), —$CH_2C(CH_3)_3$ (neo-pentyl), cyclobutyl, cyclopentyl, cyclohexyl, and cyclohexylmethyl are non-limiting examples of alkyl groups. The term "substituted alkyl" refers to a non-aromatic monovalent group with a saturated carbon atom as the point of attachment, a linear or branched, cyclo, cyclic or acyclic structure, no carbon-carbon double or triple bonds, and at least one atom independently selected from the group consisting of N, O, F, Cl, Br, I, Si, P, and S. The following groups are non-limiting examples of substituted alkyl groups: —$CH_2OH$, —$CH_2Cl$, —$CH_2Br$, —$CH_2SH$, —$CF_3$, —$CH_2CN$, —$CH_2C(O)H$, —$CH_2C(O)$ OH, —$CH_2C(O)OCH_3$, —$CH_2C(O)NH_2$, —$CH_2C(O)$ $NHCH_3$, —$CH_2C(O)CH_3$, —$CH_2OCH_3$, —$CH_2OCH_2CF_3$, —$CH_2OC(O)CH_3$, —$CH_2NH_2$, —$CH_2NHCH_3$, —$CH_2N$ $(CH_3)_2$, —$CH_2CH_2Cl$, —$CH_2CH_2OH$, —$CH_2CF_3$, —$CH_2CH_2OC(O)CH_3$, —$CH_2CH_2NHCO_2C(CH_3)_3$, and —$CH_2Si(CH_3)_3$.

The term "alkenyl" when used without the "substituted" modifier refers to a monovalent group with a nonaromatic carbon atom as the point of attachment, a linear or branched, cyclo, cyclic or acyclic structure, at least one nonaromatic carbon-carbon double bond, no carbon-carbon triple bonds, and no atoms other than carbon and hydrogen. Non-limiting examples of alkenyl groups include: —CH=$CH_2$ (vinyl), —CH=$CHCH_3$, —CH=$CHCH_2CH_3$, —$CH_2$CH=$CH_2$ (allyl), —$CH_2$CH=$CHCH_3$, and —CH=CH—$C_6H_5$. The term "substituted alkenyl" refers to a monovalent group with a nonaromatic carbon atom as the point of attachment, at least one nonaromatic carbon-carbon double bond, no carbon-carbon triple bonds, a linear or branched, cyclo, cyclic or acyclic structure, and at least one atom independently selected from the group consisting of N, O, F, Cl, Br, I, Si, P, and S. The groups, —CH=CHF, —CH=CHCl and —CH=CHBr, are non-limiting examples of substituted alkenyl groups.

The term "aryl" when used without the "substituted" modifier refers to a monovalent group with an aromatic carbon atom as the point of attachment, said carbon atom forming part of one or more six-membered aromatic ring structure(s) wherein the ring atoms are all carbon, and wherein the monovalent group consists of no atoms other than carbon and hydrogen. Non-limiting examples of aryl groups include phenyl (Ph), methylphenyl, (dimethyl)phenyl, —$C_6H_4CH_2CH_3$ (ethylphenyl), —$C_6H_4CH_2CH_2CH_3$ (propylphenyl), —$C_6H_4CH(CH_3)_2$, —$C_6H_4CH(CH_2)_2$, —$C_6H_3(CH_3)$ $CH_2CH_3$ (methylethylphenyl), —$C_6H_4$CH=$CH_2$ (vinylphenyl), —$C_6H_4$CH=$CHCH_3$, —$C_6H_4$C≡CH, —$C_6H_4$C≡$CH_3$, naphthyl, and the monovalent group derived from biphenyl. The term "substituted aryl" refers to a monovalent group with an aromatic carbon atom as the point of attachment, said carbon atom forming part of one or more six-membered aromatic ring structure(s) wherein the ring atoms are all carbon, and wherein the monovalent group further has at least one atom independently selected from the group consisting of N, O, F, Cl, Br, I, Si, P, and S. Non-limiting examples of substituted aryl groups include the groups: —$C_6H_4F$, —$C_6H_4Cl$, —$C_6H_4Br$, —$C_6H_4I$, —$C_6H_4OH$, —$C_6H_4OCH_3$, —$C_6H_4OCH_2CH_3$, —$C_6H_4OC(O)CH_3$, —$C_6H_4NH_2$, —$C_6H_4NHCH_3$, —$C_6H_4N(CH_3)_2$, —$C_6H_4CH_2OH$, —$C_6H_4CH_2OC(O)CH_3$, —$C_6H_4CH_2NH_2$, —$C_6H_4CF_3$, —$C_6H_4CN$, —$C_6H_4CHO$, —$C_6H_4CHO$, —$C_6H_4C(O)CH_3$, —$C_6H_4C(O)C_6H_5$, —$C_6H_4CO_2H$, —$C_6H_4CO_2CH_3$, —$C_6H_4CONH_2$, —$C_6H_4CONHCH_3$, and —$C_6H_4CON(CH_3)_2$.

The term "aralkyl" when used without the "substituted" modifier refers to the monovalent group -alkanediyl-aryl, in which the terms alkanediyl and aryl are each used in a manner consistent with the definitions provided above. Non-limiting examples of aralkyls are: phenylmethyl (benzyl, Bn), 1-phenyl-ethyl, 2-phenyl-ethyl, indenyl and 2,3-dihydro-indenyl, provided that indenyl and 2,3-dihydro-indenyl are only examples of aralkyl in so far as the point of attachment in each case is one of the saturated carbon atoms. When the term "aralkyl" is used with the "substituted" modifier, either one or both the alkanediyl and the aryl is substituted. Non-limiting examples of substituted aralkyls are: (3-chlorophenyl)-methyl, 2-oxo-2-phenyl-ethyl (phenylcarbonylmethyl), 2-chloro-2-phenyl-ethyl, chromanyl where the point of attachment is one of the saturated carbon atoms, and tetrahydroquinolinyl where the point of attachment is one of the saturated atoms.

The term "heteroaryl" when used without the "substituted" modifier refers to a monovalent group with an aromatic carbon atom or nitrogen atom as the point of attachment, said carbon atom or nitrogen atom forming part of an aromatic ring structure wherein at least one of the ring atoms is nitrogen, oxygen or sulfur, and wherein the monovalent group consists of no atoms other than carbon, hydrogen, aromatic nitrogen, aromatic oxygen and aromatic sulfur. Non-limiting examples of aryl groups include acridinyl, furanyl, imidazoimidazolyl, imidazopyrazolyl, imidazopyridinyl, imidazopyrimidinyl, indolyl, indazolinyl, methylpyridyl, oxazolyl, phenylimidazolyl, pyridyl, pyrrolyl, pyrimidyl, pyrazinyl, quinolyl, quinazolyl, quinoxalinyl, tetrahydroquinolinyl, thienyl, triazinyl, pyrrolopyridinyl, pyrrolopyrimidinyl, pyrrolopyrazinyl, pyrrolotriazinyl, pyrroloimidazolyl, chromenyl (where the point of attachment is one of the aromatic atoms), and chromanyl (where the point of attachment is one of the aromatic atoms). The term "substituted heteroaryl" refers to a monovalent group with an aromatic carbon atom or nitrogen atom as the point of attachment, said carbon atom or nitrogen atom forming part of an aromatic ring structure wherein at least one of the ring atoms is nitrogen, oxygen or sulfur, and wherein the monovalent group further has at least one atom independently selected from the group consisting of non-aromatic nitrogen, non-aromatic oxygen, non aromatic sulfur F, Cl, Br, I, Si, and P.

The term "heteroaralkyl" when used without the "substituted" modifier refers to the monovalent group -alkanediyl-heteroaryl, in which the terms alkanediyl and heteroaryl are each used in a manner consistent with the definitions provided above. Non-limiting examples of aralkyls are: pyridylmethyl, and thienylmethyl. When the term "heteroaralkyl" is used with the "substituted" modifier, either one or both the alkanediyl and the heteroaryl is substituted.

The term "acyl" when used without the "substituted" modifier refers to a monovalent group with a carbon atom of a carbonyl group as the point of attachment, further having a linear or branched, cyclo, cyclic or acyclic structure, further having no additional atoms that are not carbon or hydrogen, beyond the oxygen atom of the carbonyl group. The groups, —CHO, —$C(O)CH_3$ (acetyl, Ac), —$C(O)CH_2CH_3$, —$C(O)CH_2CH_2CH_3$, —$C(O)CH(CH_3)_2$, —$C(O)CH(CH_2)_2$, —$C(O)C_6H_5$, —$C(O)C_6H_4CH_3$, —$C(O)C_6H_4CH_2CH_3$, —$COC_6H_3(CH_3)_2$, and —$C(O)CH_2C_6H_5$, are non-limiting examples of acyl groups. The term "acyl" therefore encompasses, but is not limited to groups sometimes referred to as "alkyl carbonyl" and "aryl carbonyl" groups. The term "substituted acyl" refers to a monovalent group with a carbon atom of a carbonyl group as the point of attachment, further having a linear or branched, cyclo, cyclic or acyclic structure, further having at least one atom, in addition to the oxygen of the carbonyl group, independently selected from the group consisting of N, O, F, Cl, Br, I, Si, P, and S. The groups, —$C(O)CH_2CF_3$, —$CO_2H$ (carboxyl), —$CO_2CH_3$ (methylcarboxyl), —$CO_2CH_2CH_3$, —$CO_2CH_2CH_2CH_3$, —$CO_2C_6H_5$, —$CO_2CH(CH_3)_2$, —$CO_2CH(CH_2)_2$, —$C(O)NH_2$ (carbamoyl), —$C(O)NHCH_3$, —$C(O)NHCH_2CH_3$, —$CONHCH(CH_3)_2$, —$CONHCH(CH_2)_2$, —$CON(CH_3)_2$, —$CONHCH_2CF_3$, —CO-pyridyl, —CO-imidazoyl, and —$C(O)N_S$, are non-limiting examples of substituted acyl groups. The term "substituted acyl" encompasses, but is not limited to, "heteroaryl carbonyl" groups.

The term "alkoxy" when used without the "substituted" modifier refers to the group —OR, in which R is an alkyl, as that term is defined above. Non-limiting examples of alkoxy groups include: —$OCH_3$, —$OCH_2CH_3$, —$OCH_2CH_2CH_3$, —$OCH(CH_3)_2$, —$OCH(CH_2)_2$, —O-cyclopentyl, and —O-cyclohexyl. The term "substituted alkoxy" refers to the group —OR, in which R is a substituted alkyl, as that term is defined above. For example, —$OCH_2CF_3$ is a substituted alkoxy group.

Similarly, the terms "alkenyloxy", "aryloxy", "aralkoxy", "heteroaryloxy", "heteroaralkoxy" and "acyloxy", when used without the "substituted" modifier, refers to groups, defined as —OR, in which R is alkenyl, alkynyl, aryl, aralkyl, heteroaryl, heteroaralkyl and acyl, respectively, as those terms are defined above. When any of the terms alkenyloxy, alkynyloxy, aryloxy, aralkyloxy and acyloxy is modified by "substituted," it refers to the group —OR, in which R is substituted alkenyl, alkynyl, aryl, aralkyl, heteroaryl, heteroaralkyl and acyl, respectively.

The term "alkylamino" when used without the "substituted" modifier refers to the group —NHR, in which R is an alkyl, as that term is defined above. Non-limiting examples of alkylamino groups include: —$NHCH_3$, —$NHCH_2CH_3$, —$NHCH_2CH_2CH_3$, —$NHCH(CH_3)_2$, —$NHCH(CH_2)_2$, —$NHCH_2CH_2CH_2CH_3$, —$NHCH(CH_3)CH_2CH_3$, —$NHCH_2CH(CH_3)_2$, —$NHC(CH_3)_3$, —NH-cyclopentyl, and —NH-cyclohexyl. The term "substituted alkylamino" refers to the group —NHR, in which R is a substituted alkyl, as that term is defined above. For example, —$NHCH_2CF_3$ is a substituted alkylamino group.

The term "dialkylamino" when used without the "substituted" modifier refers to the group —NRR', in which R and R' can be the same or different alkyl groups, or R and R' can be taken together to represent an alkanediyl having two or more saturated carbon atoms, at least two of which are attached to the nitrogen atom. Non-limiting examples of dialkylamino groups include: —$NHC(CH_3)_3$, —$N(CH_3)CH_2CH_3$, —$N(CH_2CH_3)_2$, N-pyrrolidinyl, and N-piperidinyl. The term "substituted dialkylamino" refers to the group —NRR', in which R and R' can be the same or different substituted alkyl groups, one of R or R' is an alkyl and the other is a substituted alkyl, or R and R' can be taken together to represent a substituted alkanediyl with two or more saturated carbon atoms, at least two of which are attached to the nitrogen atom.

The terms "alkoxyamino", "alkenylamino", "arylamino", "aralkylamino", "heteroarylamino", "heteroaralkylamino", and "alkylsulfonylamino" when used without the "substituted" modifier, refers to groups, defined as —NHR, in which R is alkoxy, alkenyl, alkynyl, aryl, aralkyl, heteroaryl, heteroaralkyl and alkylsulfonyl, respectively, as those terms are defined above. A non-limiting example of an arylamino group is —NHC$_6$H$_5$. When any of the terms alkoxyamino, alkenylamino, alkynylamino, arylamino, aralkylamino, heteroarylamino, heteroaralkylamino and alkylsulfonylamino is modified by "substituted," it refers to the group —NHR, in which R is substituted alkoxy, alkenyl, alkynyl, aryl, aralkyl, heteroaryl, heteroaralkyl and alkylsulfonyl, respectively.

The term "amido" (acylamino), when used without the "substituted" modifier, refers to the group —NHR, in which R is acyl, as that term is defined above. A non-limiting example of an acylamino group is —NHC(O)CH$_3$. When the term amido is used with the "substituted" modifier, it refers to groups, defined as —NHR, in which R is substituted acyl, as that term is defined above. The groups —NHC(O)OCH$_3$ and —NHC(O)NHCH$_3$ are non-limiting examples of substituted amido groups.

In addition, atoms making up the compounds of the present invention are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}$C and $^{14}$C. Similarly, it is contemplated that one or more carbon atom(s) of a compound of the present invention may be replaced by a silicon atom(s). Furthermore, it is contemplated that one or more oxygen atom(s) of a compound of the present invention may be replaced by a sulfur or selenium atom(s).

Any undefined valency on an atom of a structure shown in this application implicitly represents a hydrogen atom bonded to the atom.

As used herein, a "chiral auxiliary" refers to a removable chiral group that is capable of influencing the stereoselectivity of a reaction. Persons of skill in the art are familiar with such compounds, and many are commercially available.

The use of the word "a" or "an," when used in conjunction with the term "comprising" in the claims and/or the specification may mean "one," but it is also consistent with the meaning of "one or more," "at least one," and "one or more than one."

Throughout this application, the term "about" is used to indicate that a value includes the inherent variation of error for the device, the method being employed to determine the value, or the variation that exists among the study subjects.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

The term "effective," as that term is used in the specification and/or claims, means adequate to accomplish a desired, expected, or intended result.

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

"Effective amount," "Therapeutically effective amount" or "pharmaceutically effective amount" means that amount which, when administered to a subject or patient for treating a disease, is sufficient to effect such treatment for the disease.

The above definitions supersede any conflicting definition in any of the reference that is incorporated by reference herein. The fact that certain terms are defined, however, should not be considered as indicative that any term that is undefined is indefinite. Rather, all terms used are believed to describe the invention in terms such that one of ordinary skill can appreciate the scope and practice the present invention.

VI. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Diastereo- and Enantioselective Bis(Amidine)-Catalyzed Aryl Nitromethane Addition to Azomethine Nitroalkane 9 was prepared in one step from para-chlorobenzyl chloride using the method of Kornblum et al. (1956) and imine 8 was formed from the corresponding α-amido sulfone using potassium carbonate to effect the elimination to azomethine (Marianacci et al., 2007). For example, it was possible to promote the addition of nitroalkane 9 to imine 8 utilizing a symmetrical chiral proton catalyst (10.HOTf), leading to the adduct in >20:1 dr and 66% ee (major). See Table 1, entry 1. below. Part of the basis for this approach and examples for how this approach may be further modified are provided by (Davis et al., 2010; Shen and Johnston, 2008; Nugent et al., 2004), which are incorporated herein by reference.

Use of the free base was also investigated. Use of bis (amidine) 10 under otherwise identical conditions led to product with equal diastereoselection and enantioselection. See Table 1, entry 2. It is noted that protonation of the Brønsted basic bis(amidine) by Brønsted acidic aryl nitromethane 9 is possible, and the aryl nitromethane salt that results (e.g., [BAM·H$_2$]$^{2+}$·[TfO]$^-$[ArCHNO$_2$]$^-$) could itself be a catalyst in these reactions.

Also investigated were both free base and 1:1 BAM:TfOH. Using unsymmetrical ligand 11, it was found that the salt led to the desired addition product with good diastereoselection (13:1 dr), and slightly improved enantioselection (72% ee) (Table 1, entry 3), whereas the free base was more diastereoselective (>20:1 dr), but less enantioselective (53% ee) (Table 1, entry 4). The binding pocket in catalyst 12 may be more open than those of the two previous ligands (10-11), leading to low enantioselection while the diastereoselection remained high (Table 1, entries 5-6). However, the free base provided enantioselection at a slightly improved level relative to the use of its triflic acid salt, emphasizing the need to optimize this transformation using a rather empirical approach. It was not until the Pyrrolidine Bis(amidine) (13a) (see Davis et al., 2010) was used that the enantioselection increased significantly to 85% ee (Table 1, entry 7).

The behavior of this bis(amidine) was consistent with its parent HQuin-BAM (10) in that the free base performed equally well relative to the triflic acid salt (Table 1, cf. entries 7-8). Due to the increase in enantioselection upon increasing the Brønsted basicity/electron rich nature of the aromatic rings, the inventors prepared three additional derivatives in which the quinoline periphery is substituted by methoxy groups (13b-d). These catalysts provided slight improvements over 13a, with 13d leading to the addition product in 13:1 dr, 91% ee, and nearly quantitative yield (Table 1, entries 9-11). A single fractional recrystallization of this material from toluene provided the adduct as a single diastereomer (>200:1) with 97% ee (98.5:1.5 enantiomeric ratio).

TABLE 1

Development of a Diastereo- and Enantioselective Bis(amidine)-Catalyzed Aryl Nitromethane Addition to Azomethine.

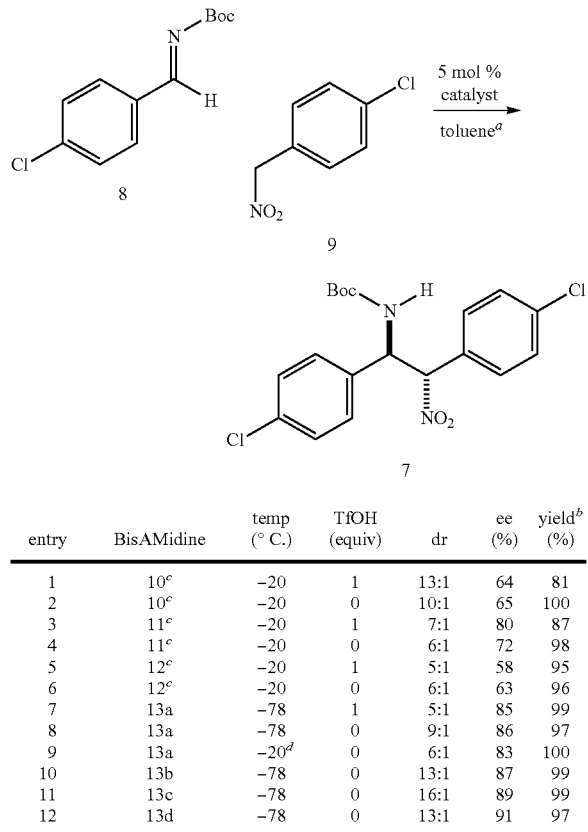

| entry | BisAMidine | temp (° C.) | TfOH (equiv) | dr | ee (%) | yield[b] (%) |
|---|---|---|---|---|---|---|
| 1 | 10[c] | −20 | 1 | 13:1 | 64 | 81 |
| 2 | 10[c] | −20 | 0 | 10:1 | 65 | 100 |
| 3 | 11[c] | −20 | 1 | 7:1 | 80 | 87 |
| 4 | 11[c] | −20 | 0 | 6:1 | 72 | 98 |
| 5 | 12[c] | −20 | 1 | 5:1 | 58 | 95 |
| 6 | 12[c] | −20 | 0 | 6:1 | 63 | 96 |
| 7 | 13a | −78 | 1 | 5:1 | 85 | 99 |
| 8 | 13a | −78 | 0 | 9:1 | 86 | 97 |
| 9 | 13a | −20[d] | 0 | 6:1 | 83 | 100 |
| 10 | 13b | −78 | 0 | 13:1 | 87 | 99 |
| 11 | 13c | −78 | 0 | 16:1 | 89 | 99 |
| 12 | 13d | −78 | 0 | 13:1 | 91 | 97 |

Figure 5:
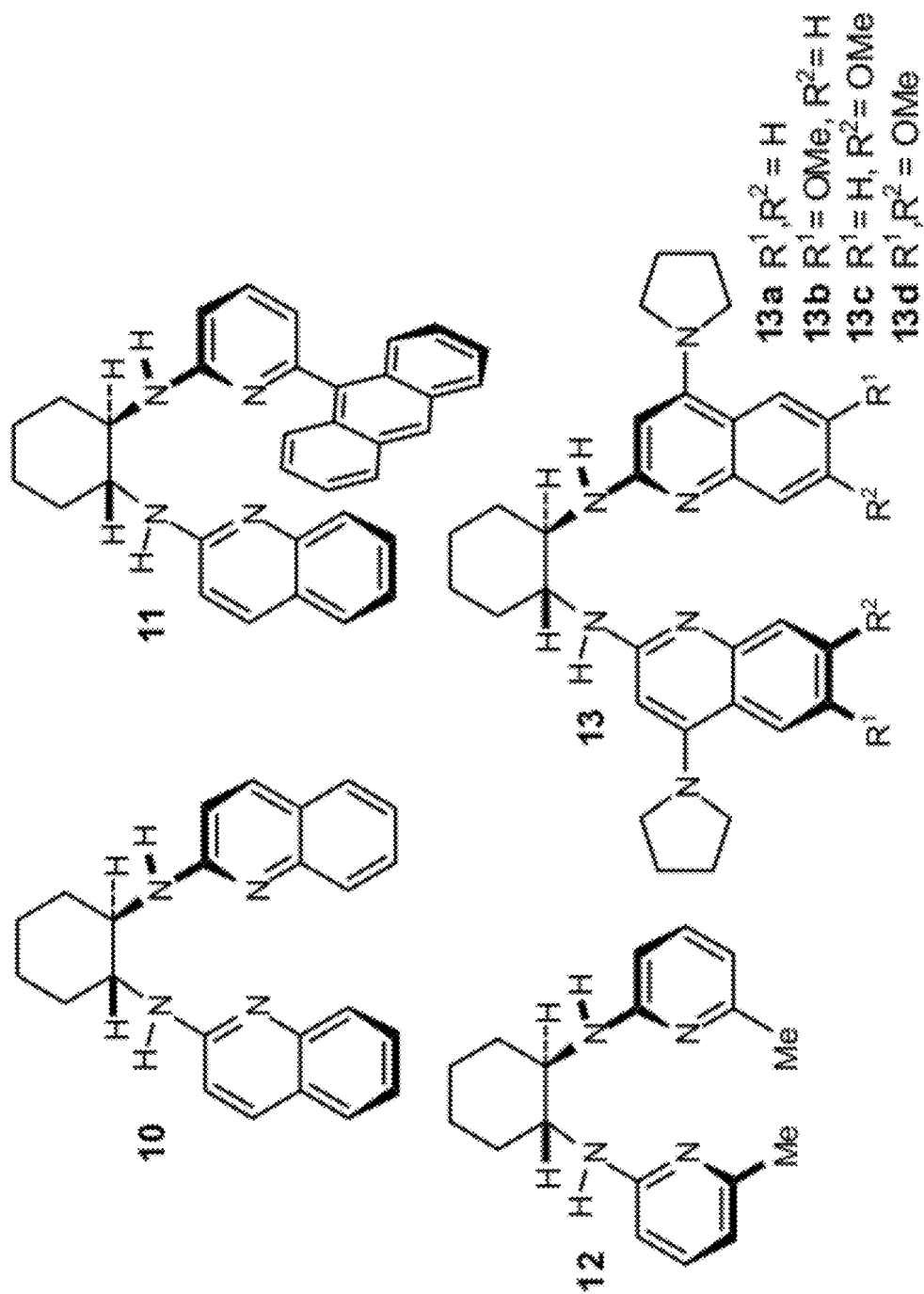
FIG. 5—Bis(amidine) Catalysts. This scheme shows the chemical formulas of the bis(amidine) catalysts of Table 1.

Structures for the bisAmide catalysts are shown in FIG. 5.
[a]All reactions used 1.1 equiv of 9 (0.1-0.2 mmol) in toluene (0.1M) with a 24 h reaction time unless otherwise noted. Assignment of configuration for 7, was accomplished in the manner described below. Diastereomer ratio (dr) and enantiomeric excess (ee) were determined by HPLC.
[b]Isolated yield after column chromatography.
[c]10 mol % catalyst used, 48 h reaction time.
[d]2 h reaction time.

Example 2

Synthesis of Bis(amidine) Catalysts and Diastereo- and Enantioselective Synthesis of (−)-Nutlin-3

In order to avoid a meso intermediate without unduly telescoping the synthesis using deprotection techniques, the conversion of the β-amino nitroalkane into the unsymmetrical imidazoline uses the inherent chemoselectivity offered by this intermediate. In this embodiment this was accomplished by reduction of the nitro to amine using cobalt boride formed in situ (Satoh et al., 1969), and subsequent acylation with acid 14 to produce Boc-protected amide 15 (FIG. 3). Straightforward deprotection of the Boc group using trifluoroacetic acid revealed the secondary amine in 88% yield. Acylation of the amine with carbonyl diimidazole led to an intermediate isocyanate that was treated with piperazinone 16.

This set the stage to attempt a chemoselective cyclizative dehydration to the desired imidazoline. For this purpose, the inventors turned to the powerful dehydrating property of a phosphonium anhydride formed by the combination of triphenyl phosphine oxide and triflic anhydride. This protocol was described by Hendrickson, who demonstrated its use in a variety of amide dehydrative cyclizations (Hendrickson and Schwartzman, 1975; Hendrickson and Hussoin, 1989; Hendrickson and Hussoin, 1987). Examples of heterocycle formation using this reagent has been described in several contexts. See (You and Kelly, 2004; You et al., 2003; Petersson et al., 2009; Petersson et al., 2008), which are incorporated herein by references. Disclosed herein is its apparently unprecedented chemoselectivity toward amide and carbamate carbonyls appears. Faced with the context of mixed amide/carbamate 17, the Hendrickson protocol was applied and a single imidazoline product was observed that was retrieved in 88% isolated yield.

The exact mass for Nutlin-3 was determined by high resolution mass spectrometry. Evidence was obtained to support whether the desired imidazoline (Nutlin-3) or an alternative isomer (18) formed during this dehydrative cyclization. Support for the imidazoline depicted for Nutlin-3 was obtained by an HMBC (600 MHz) experiment. Among the $^3J_{HC}$ couplings observed was the diagnostic crosspeak to the urea carbon from H1 of the imidazoline; a crosspeak between H8 and an amide carbonyl carbon was not observed (FIG. 4). Nutlin-3 produced using this synthesis and catalyst 13 is levorotatory (U.S. Publn. 2005/282803).

The absolute configuration was assigned here by analogy to all other cases using nitroalkanes and bis(amidine) catalysts. See Davis et al. (2010), Shen and Johnston (2008), and Nugent et al. (2004), each of which are incorporated by reference herein.

The details are as follows: All reagents and solvents were commercial grade and purified prior to use when necessary. The following reagents were used as supplied by Sigma-Aldrich without further purification except when noted otherwise. Aldimines were prepared as reported in the literature. See Kanazawa et al., 1994, which is incorporated herein by reference. 2,4-Dichloro-6,7-dimethoxyquinoline was prepared with a procedure similar to that of 2,4-dichloro-6-methoxyquinoline and 2,4-dichloro-7-methoxyquinoline (see below). Toluene was dried by passage through a column of activated alumina as described by Pangborn et al. (1996), which is incorporated herein by reference. Thin layer chromatography (TLC) was performed using glass-backed silica gel (250 μm) plates and flash chromatography utilized 230-400 mesh silica gel from Sorbent Technologies. UV light, and/or the use of potassium iodoplatinate and potassium permanganate solutions were used to visualize products. IRA-900-$NO_2$ resin was prepared by washing IRA900-Cl resin with aq $NaNO_2$ until the wash no longer tested positive for chloride by a $AgNO_3$ test.

Nuclear magnetic resonance spectra (NMR) were acquired on a Bruker DRX-500 (500 MHz), Bruker AV-400 (400 MHz) or Bruker AV II-600 (600 MHz) instrument. Chemical shifts are measured relative to residual solvent peaks as an internal standard set to δ 7.26 and δ 77.0 ($CDCl_3$). IR spectra were recorded on a Thermo Nicolet IR100 spectrophotometer and are reported in wavenumbers ($cm^{-1}$). Compounds were analyzed as neat films on a NaCl plate (transmission). Mass spectra were recorded on a Waters LCT spectrometer by use of the ionization method noted.

Absolute and relative configuration of 7 was assigned by analogy to tert-butyl (1r,2s)-1-(4-bromo-3-methoxyphenyl)-2-nitro-2-phenylethylcarbamate, for which a crystal structure was obtained.

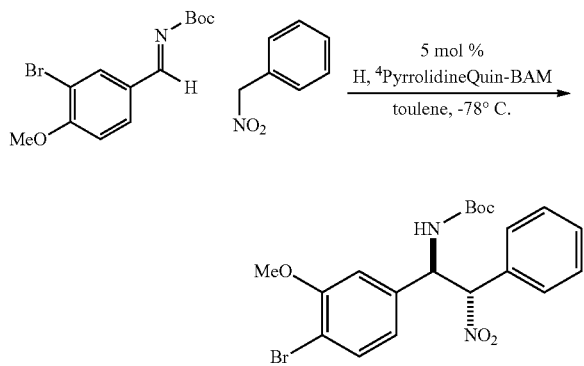

tert-butyl (1R2S)-1-(4-bromo-3-methoxyphenyl)-2-nitro-2-phenylethyl-carbamate. tert-Butyl 3-bromo-4-methoxybenzylidenecarbamate (62.8 mg, 200 µmol) and H,4PyrrolidineQuin-BAM (5.1 mg, 10 µmol) were dissolved in toluene (2 mL) at room temperature. The solution was chilled to −78° C. before addition of nitromethylbenzene (41.1 mg, 300 µmol). The reaction was then stirred at −78° C. for 20 h. The reaction was kept at the reaction temperature until filtered through a pad of silica with $CH_2Cl_2$ and EtOAc. The filtrate was concentrated and then purified by column chromatography (5-40% ethyl acetate in hexanes) to afford a white solid (67.1 mg, 74%) that was found to be 73% ee by chiral HPLC; (Chiralcel IA, 5% iPrOH/hexanes, 1 mL/min, $t_r$(anti, major)= 61.8 min, $t_r$(anti, minor)=29.2 min, $t_r$(syn, major)=26.8 min, $t_r$(syn, minor)=49.6 min); Mp 157.0-159.0° C.; $R_f$=0.19 (20% EtOAc/hexanes); IR (film) 3387, 2979, 1685, 1553 cm$^{-1}$; $^1$H NMR (400 MHz, CDCl$_3$) δ 7.55 (dd, J=7.2, 2.0 Hz, 2H), 7.53 (d, J=2.0 Hz, 1H), 7.46-7.38 (m, 3H), 7.30-7.25 (dd, J=8.4, 2.0 Hz, 1H), 6.86 (d, J=8.4 Hz, 1H), 5.72 (d, J=10.0 Hz, 1H), 5.58 (dd, J=9.2, 9.2 Hz, 1H), 4.77 (d, J=8.8 Hz, 1H), 3.89 (s, 3H), 1.26 (s, 9H); $^{13}$C NMR (150 MHz, CDCl$_3$) ppm 156.1, 154.1, 131.9, 131.3, 131.1, 130.3, 128.9, 128.7, 127.7, 112.1, 112.0, 94.1, 80.5, 56.2, 55.8, 28.0; HRMS (ESI): Exact mass calcd for $C_{20}H_{23}BrN_2NaO_5$ [M+Na]$^+$ 473.0688. found 473.0711.

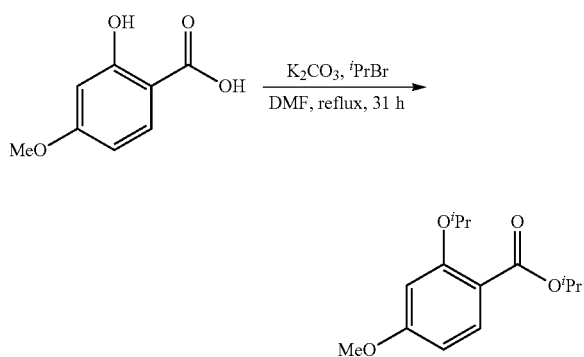 [SMILES: COc1ccc(C(=O)O)c(O)c1 ; COc1ccc(C(=O)OC(C)C)c(OC(C)C)c1]

isopropyl 2-isopropoxy-4-methoxybenzoate. See Hattori et al., 2003, which is incorporated herein by reference. Iso-propyl bromide (2.926 g, 23.79 mmol) was added to a stirred mixture of 4-methoxysalicylic acid (1.000 g, 5.947 mmol), K$_2$CO$_3$ (3.286 g, 23.79 mmol), and dry DMF (30 mL) at room temperature. The mixture was allowed to stir for 20 min before heating to reflux for 31 h. The reaction mixture was cooled to room temperature, treated with KI (98.7 mg, 595 µmol) and stirred for 17 h. The reaction was quenched with 1 M aq HCl then extracted with diethyl ether. The combined organic layers were washed with 1 M aq Na$_2$CO$_3$, water, then brine before drying over MgSO$_4$. Concentration of the dried organic layers resulted in a bronze oil (1.0549 g, 70%) that was pure by $^1$H NMR. $R_f$=0.16 (5% EtOAc/hexanes); IR (film) 2979, 2936, 1721, 1694, 1608, 1575 cm$^{-1}$; $^1$H NMR (400 MHz, CDCl$_3$) δ 7.77 (d, J=7.2 Hz, 1H), 6.49-6.43 (m, 2H), 5.20 (heptet, J=6.4 Hz, 1H), 4.55 (heptet, J=6.0 Hz, 1H), 3.81 (s, 3H), 1.36 (d, J=6.0 Hz, 6H), 1.33 (d, J=6.0 Hz, 6H); $^{13}$C NMR (100 MHz, CDCl$_3$) ppm 165.8, 163.5, 159.3, 133.4, 114.9, 104.9, 101.8, 71.5, 67.5, 55.4, 22.0 (2C); HRMS (CI): Exact mass calcd for $C_{14}H_{21}O_4$[M+H]$^+$ 253.1434. found 253.1431.

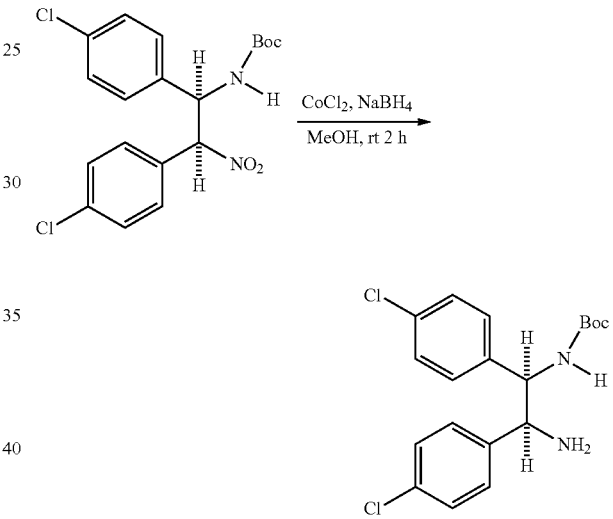

tert-butyl (1R,2S)-2-amino-1,2-bis(4-chlorophenyl)ethyl-carbamate. The nitroalkane (411.3 mg, 1.000 mmol) was dissolved in MeOH (4.0 mL) at room temperature. CoCl$_2$ (129.8 mg, 1.000 mmol) was added and the reaction mixture was chilled to 0° C. before NaBH$_4$ (567.6 mg, 15.00 mmol) was added in three portions over 40 min. The reaction mixture was stirred at 0° C. for an additional 30 min before the mixture was quenched with sat. aq. NH$_4$Cl. The reaction mixture was adjusted to pH 10 with conc. aq. NH$_4$OH. The mixture was extracted with ethyl acetate, dried over MgSO$_4$, and concentrated. Column chromatography (25-45% ethyl acetate in hexanes) of the residue afforded the product as a white solid (251.7 mg, 66%). Mp 149.0-150.0° C.; [α]$_D^{20}$ +67 (c 0.12, CHCl$_3$); $R_f$=0.12 (50% EtOAc/hexanes); IR (film) 3377, 2981, 1683, 1523 cm$^{-1}$; $^1$H NMR (400 MHz, CDCl$_3$) δ 7.24 (d, J=8.4 Hz, 2H), 7.21 (d, J=8.4 Hz, 2H), 7.00 (d, J=8.4 Hz, 2H), 6.93 (d, J=8.4 Hz, 2H), 5.49 (d, J=7.6 Hz, 1H), 4.79 (br s, 1H), 4.23 (br s, 1H), 1.50 (s, 2H), 1.36 (s, 9H); $^{13}$C NMR (100 MHz, CDCl$_3$) ppm 155.0, 140.3 (2C), 133.3, 133.2, 128.7, 128.4, 128.2 (2C), 79.8, 59.5, 59.1, 28.2; HRMS (ESI): Exact mass calcd for $C_{19}H_{23}Cl_2N_2O_2$[M+H]$^+$381.1137. found 381.1147.

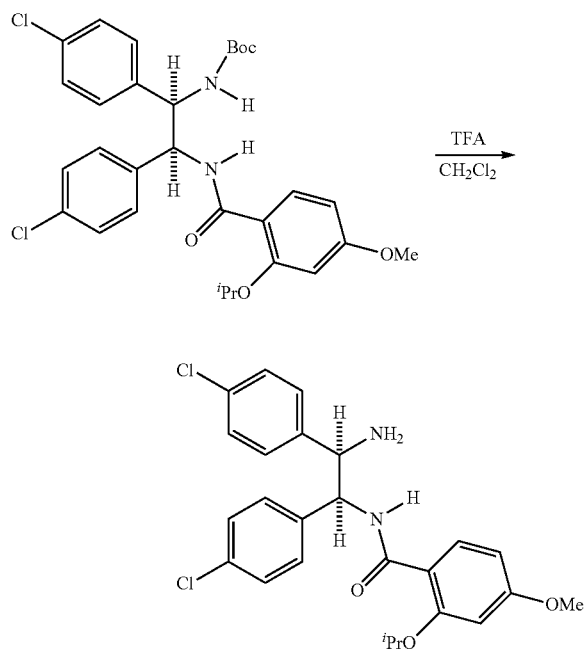

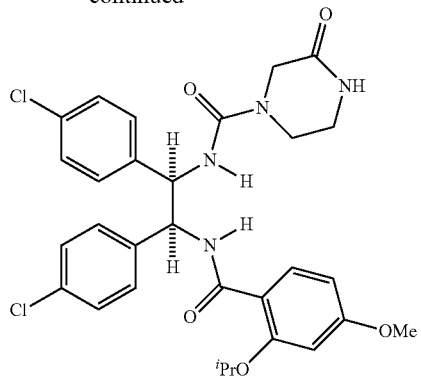

N-((1S,2R)-2-AMINO-1,2-BIS(4-CHLOROPHENYL) ETHYL)-2-ISOPROPOXY-4-METHOXYBENZAMIDE.

Amide (180.0 mg, 313.9 μmol) was dissolved in $CH_2Cl_2$ (3.1 mL)

TFA (932 μL, 12.6 mmol) was added and the mixture was stirred at room temperature for 16 h. The reaction mixture was poured into satd. aq. $NaHCO_3$ and extracted with $CH_2Cl_2$. The combined organic layers were dried over $MgSO_4$, filtered, and concentrated to a light brown foam (130.3 mg, 88%). $[\alpha]_D^{20}$ −140 (c 0.11, $CHCl_3$); $R_f$=0.46 (10% MeOH/$CH_2Cl_2$); IR (film) 3376, 2925, 2853, 1644, 1605, 1521 cm$^{-1}$; $^1$H NMR (400 MHz, $CDCl_3$) δ 8.88 (d, J=8.0 Hz, 1H), 8.13 (d, J=8.8 Hz, 1H), 7.24 (d, J=8.4 Hz, 2H), 7.20 (d, J=8.4 Hz, 2H), 7.03 (d, J=8.4 Hz, 2H), 7.00 (d, J=8.8 Hz, 2H), 6.56 (dd, J=8.8, 2.4 Hz, 1H), 6.49 (d, J=2.0 Hz, 1H), 5.43 (dd, J=8.0, 4.8 Hz, 1H), 4.75 (qq, J=6.0, 6.0 Hz, 1H), 4.41 (d, J=4.8 Hz, 1H), 3.83 (s, 3H), 1.45 (d, J=5.6 Hz, 3H), 1.44 (d, J=5.6 Hz, 3H); $^{13}$C NMR (100 MHz, $CDCl_3$) ppm 164.7, 163.3, 157.2, 140.7, 136.8, 134.1, 133.2, 133.1, 129.1, 128.4, 128.3, 128.2, 115.0, 105.1, 100.3, 71.5, 59.0, 58.6, 55.5, 22.2, 22.0; HRMS (ESI): Exact mass calcd for $C_{25}H_{27}Cl_2N_2O_3$ [M+H]$^+$ 473.1399. found 473.1400.

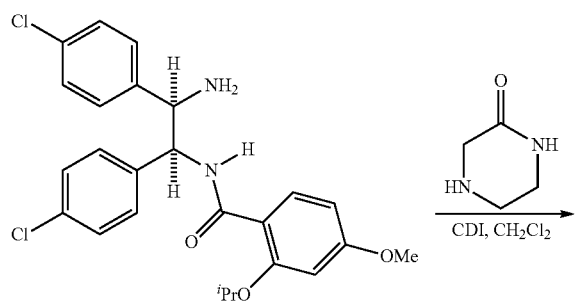

N-((1R,2S)-1,2-BIS(4-CHLOROPHENYL)-2-(2-ISO-PROPOXY-4-METHOXYBENZAMIDO)ETHYL)-3-OX-OPIPERAZINE-1-CARBOX-AMIDE.

Amine (100.0 mg, 211.2 μmol) was dissolved in $CH_2Cl_2$ (1.0 mL) and stirred at room temperature. CDI (41.1 mg, 253.5 μmol) was added and the reaction was stirred for 1 h. 2-Oxo-piperazine (42.3 mg, 422.4 μmol) was added, and the reaction mixture was stirred for an additional 4 hours. The reaction mixture was concentrated and purified by column chromatography (0-2-5% methanol in dichloromethane) to provide a white solid (119.6 mg, 94%). $[\alpha]_D^{20}$ +110 (c 0.14, $CHCl_3$); $R_f$=0.34 (10% MeOH/$CH_2Cl_2$); IR (film) 3369, 2978, 2932, 2243, 1634, 1605 cm$^{-1}$; $^1$H NMR (400 MHz, $CDCl_3$) δ 8.37 (d, J=8.0 Hz, 1H), 8.28 (d, J=8.8 Hz, 1H), 7.80 (d, J=4.8 Hz, 1H), 7.29 (d, J=8.4 Hz, 2H), 7.17 (d, J=8.4 Hz, 2H), 6.95 (d, J=8.4 Hz, 2H), 6.88 (d, J=8.4 Hz, 2H), 6.62 (dd, J=8.8, 2.0 Hz, 1H), 6.46 (d, J=2.0 Hz, 1H), 6.15 (br s, 1H), 5.77 (dd, J=7.6, 2.0 Hz, 1H), 5.10 (dd, J=8.8, 2.4 Hz, 1H), 4.66 (qq, J=6.0, 6.0 Hz, 1H), 4.15 (d, J=2.4 Hz, 2H), 3.86 (s, 3H), 3.73 (ddd, J=13.2, 5.6, 4.4 Hz, 1H), 3.60 (ddd, J=13.2, 6.4, 4.4 Hz, 1H), 3.46-3.35 (m, 2H), 1.20 (d, J=6.0 Hz, 3H), 1.14 (d, J=6.0 Hz, 3H); $^{13}$C NMR (100 MHz, $CDCl_3$) ppm 168.0, 167.0, 163.0, 157.2, 155.9, 136.7, 136.6, 134.3, 133.8, 133.2, 129.4, 128.6, 128.4, 128.0, 113.5, 105.4, 100.3, 71.4, 61.6, 57.5, 55.5, 47.4, 40.9, 39.9, 21.9, 21.5; HRMS (CI): Exact mass calcd for $C_{30}H_{33}Cl_2N_4O_5$ [M+H]$^+$ 599.1823. found 599.1814.

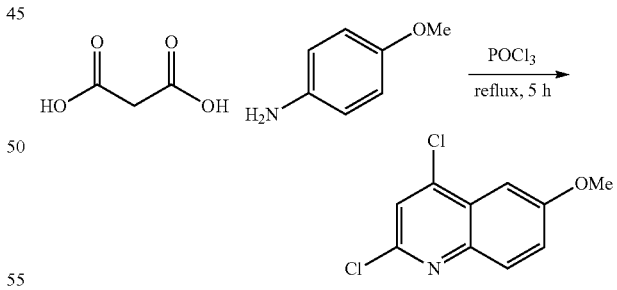

2,4-DICHLORO-6-METHOXYQUINOLINE.

Phosphorus(V)oxychloride (40 mL, 1.5 M) was added through a condenser into a 3-neck round bottom flask containing malonic acid (6.244 g, 60.00 mmol) and a stir bar at room temperature. While stirring, p-anisidine (9.236 g, 75.00 mmol) was added in small portions over a period of 15 minutes through an open neck of the round bottom flask. The reaction mixture was heated and stirred at reflux for 5 hours. The reaction mixture was allowed to cool to room temperature before it was poured over crushed ice (~700 mL). The pH of the resulting aqueous solution was then adjusted to 10 with concentrated ammonium hydroxide (~85 mL). The aqueous suspension was extracted with dichloromethane. The combined organic layers were then dried over MgSO$_4$ before concentration. Purification by column chromatography (0-5% ethyl acetate in hexanes) yielded the title compound as a slightly yellow solid (4.7812 g, 35%). Mp 170.5-171.5° C.; R$_f$=0.27 (2% EtOAc/hexanes); IR (film) 3084, 3013, 2982, 1623, 1562, 1499 cm$^{-1}$; $^1$H NMR (500 MHz, CDCl$_3$) δ 7.90 (d, J=9.0 Hz, 1H), 7.45 (s, 1H), 7.40 (dd, J=9.0, 3.0 Hz, 1H), 7.36 (d, J=3.0 Hz, 1H), 3.96 (s, 3H); $^{13}$C NMR (125 MHz, CDCl$_3$) ppm 158.9, 147.0, 144.0, 142.6, 130.4 126.3, 124.1, 122.0, 101.9, 55.7; HRMS submitted.

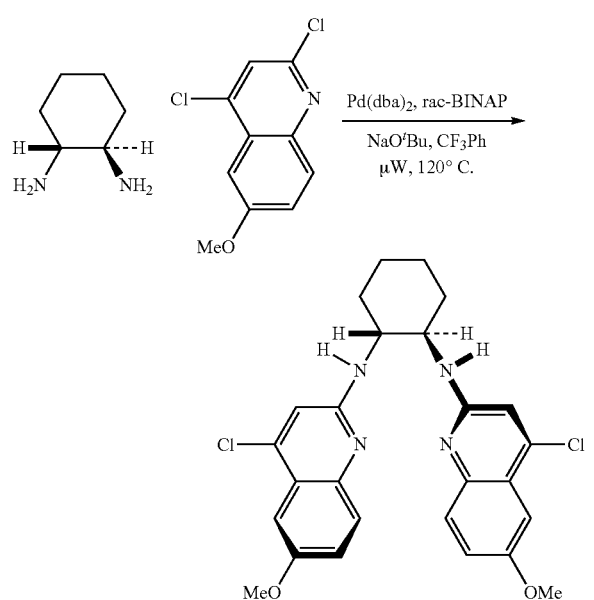

H,$^4$CL$^6$MEOQUIN-BAM. A 2-5 mL μW vial was charged with (R,R)-diaminocyclohexane (125.2 mg, 1.096 mmol), 2,4-dichloro-6-methoxyquinoline (500 mg, 2.190 mmol), Pd(dba)$_2$ (12.6 mg, 22.0 μmol), rac-BINAP (13.6 mg, 22.0 μmol), and sodium tert-butoxide (316.2 mg, 3.290 mmol). See Wagaw et al., 1997, which is incorporated herein by reference. Trifluoromethylbenzene (3.8 mL) was added and the resulting suspension was heated at 120° C. and stirred in the microwave for 10 min. The reaction mixture was triturated with CH$_2$Cl$_2$ and filtered. The filtrate was concentrated and purified by column chromatography (10-20% ethyl acetate in hexanes) to provide a yellow solid (420.3 mg, 77%) that was pure by $^1$H NMR; [α]$_D^{20}$ +610 (c 0.18, CHCl$_3$); R$_f$=0.18 (20% EtOAc/hexanes); IR (film) 3218, 2925, 1605, 1495 cm$^{-1}$; $^1$H NMR (600 MHz, CDCl$_3$, 325 K) δ 7.64 (d, J=9.0 Hz, 2H), 7.30 (d, J=3.0 Hz, 2H), 7.25 (dd, J=9.0, 3.0 Hz, 2H), 6.38 (br s, 2H), 5.72 (br s, 2H), 4.05-3.90 (m, 2H), 3.91 (s, 6H), 2.39-2.25 (m, 2H), 1.90-1.80 (m, 2H), 1.55-1.35 (m, 4H); $^{13}$C NMR (150 MHz, CDCl$_3$, 325 K) ppm 155.5, 155.4, 144.0, 141.4, 127.6, 121.9, 121.8, 111.8, 103.7, 56.1, 55.6, 33.0, 24.9; HRMS (ESI): Exact mass calcd for C$_{26}$H$_{27}$Cl$_2$N$_4$O$_2$ [M+H]$^+$ 497.1511. found 497.1500.

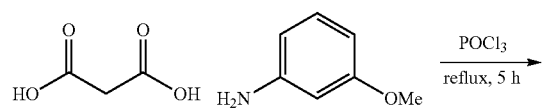

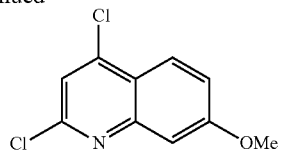

2,4-DICHLORO-7-METHOXYQUINOLINE. Phosphorus(V)oxychloride (20 mL, 1.3 M) was added through a running condenser into a 3-neck round bottom flask equipped with a stir bar containing malonic acid (2.710 g, 26.00 mmol) at room temperature. While stirring, m-anisidine (4.000 g, 32.48 mmol) was added in small portions over a period of 15 minutes through an open neck of the round bottom flask. The reaction mixture was heated and stirred at reflux for 5 hours. The reaction mixture was allowed to cool to room temperature before it was poured over crushed ice (~350 mL). The pH of the resulting aqueous solution was adjusted to 10 with concentrated ammonium hydroxide. The aqueous suspension was extracted with dichloromethane. The combined organic layers were dried over MgSO$_4$ and filtered before concentration to provide a 2.2:1 mixture ($^1$H NMR) of the 7-methoxy and 5-methoxy regioisomers. Purification by column chromatography (0-8% ethyl acetate in hexanes) yielded a white solid (3.181 g, 54%) that was recrystallized from ethyl acetate and hexanes to provide the 7-methoxy isomer. Mp 131.5-132.5° C.; R$_f$=0.18 (5% EtOAc/hexanes); IR (film) 3092, 2982, 1623, 1572, 1559 cm$^{-1}$; $^1$H NMR (400 MHz, CDCl$_3$) δ 8.01 (d, J=9.2 Hz, 1H), 7.32 (s, 1H), 7.31 (d, J=2.4 Hz, 1H), 7.23 (dd, J=9.2, 2.4 Hz, 1H), 3.92 (s, 3H); $^{13}$C NMR (100 MHz, CDCl$_3$) ppm 162.2, 150.2, 150.0, 143.9, 125.2, 120.7, 120.1, 119.5, 107.1, 55.7; HRMS submitted.

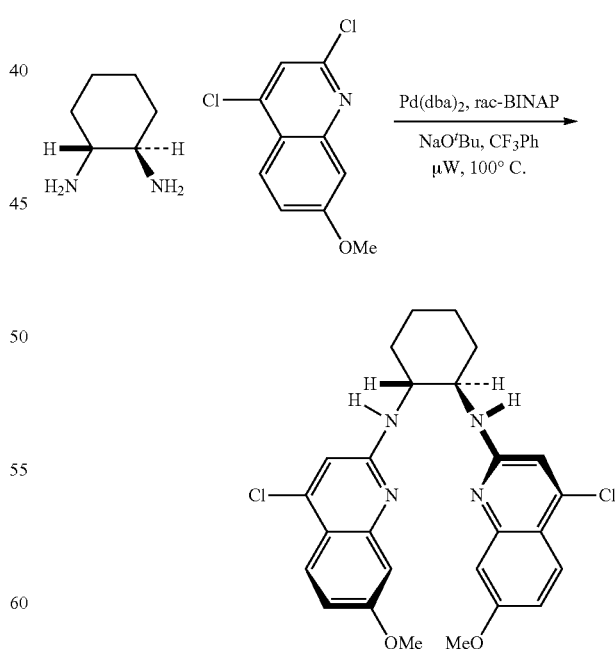

H,4CL7MEOQUIN-BAM. A 2-5 mL μW vial was charged with (R,R)-diaminocyclohexane (125.2 mg, 1.096 mmol), 2,4-dichloro-7-methoxyquinoline (500 mg, 2.190 mmol), Pd(dba)$_2$ (12.6 mg, 22.0 μmol), rac-BINAP (13.6 mg, 22.0

μmol), and sodium tert-butoxide (316.2 mg, 3.290 mmol). Trifluoromethylbenzene (3.8 mL) was added and the resulting suspension was heated at 100° C. and stirred in the microwave for 10 min. The reaction mixture was diluted with $CH_2Cl_2$ and filtered through Celite. The filtrate was concentrated and washed with $CH_2Cl_2$ then hexanes to provide a light brown powder (412.9 mg, 76%) that was pure by $^1H$ NMR; $[\alpha]_D^{20}$ +580 (c 0.19, $CHCl_3$); $R_f$=0.25 (50% EtOAc/hexanes); IR (film) 3220, 2933, 1610, 1510 $cm^{-1}$; $^1H$ NMR (500 MHz, $CDCl_3$, 325 K) δ 7.82 (d, J=9.0 Hz, 2H), 7.08 (s, 2H), 6.91 (dd, J=9.0, 2.5 Hz, 2H), 6.31 (br s, 2H), 5.64 (br s, 2H), 4.09 (br s, 2H), 3.94 (s, 6H), 2.41-2.32 (m, 2H), 1.90-1.80 (m, 2H), 1.55-1.38 (m, 4H); $^{13}C$ NMR (100 MHz, $CDCl_3$, 325 K) ppm 162.0, 157.3, 150.5, 142.3, 125.3, 116.3, 114.4, 109.5, 106.0, 56.1, 55.5, 32.9, 24.9; HRMS (ESI): Exact mass calcd for $C_{26}H_{27}Cl_2N_4O_2$ $[M+H]^+$ 497.1511. found 497.1501.

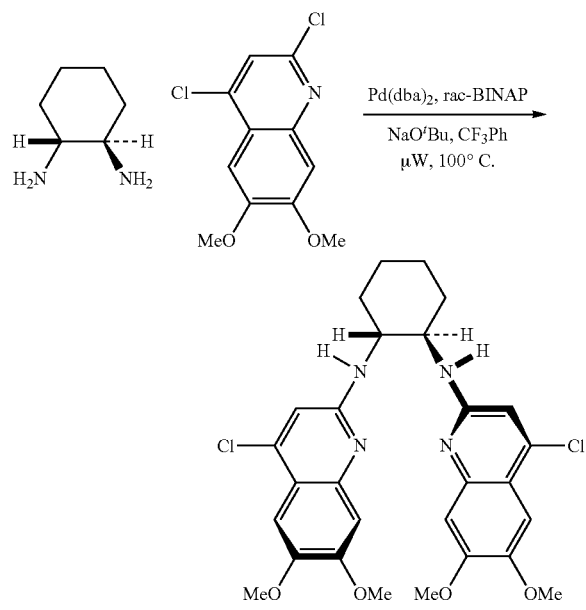

H,$^4$CL$^{6,7}$(MEO)$_2$QUIN-BAM. A 10-20 mL μW vial was charged with (R,R)-diaminocyclohexane (442.4 mg, 3.874 mmol), 2,4-dichloro-6,7-dimethoxyquinoline (2.000 g, 7.749 mmol), Pd(dba)$_2$ (44.5 mg, 77.48 μmol), rac-BINAP (48.2 mg, 77.48 μmol), and sodium tert-butoxide (1.117 g, 11.62 mmol). Trifluoromethylbenzene (13.4 mL) was added and the resulting suspension was heated at 100° C. and stirred in the microwave for 10 min. The reaction mixture was filtered through celite with $CH_2Cl_2$ and concentrated. The residue was triturated with ethyl acetate and hexanes to provide a light brown powder (1.4612 g, 68%) that was sufficiently pure by $^1H$ NMR; $[\alpha]_D^{20}$ +410 (c 0.10, $CHCl_3$); $R_f$=0.15 (50% EtOAc/hexanes); IR (film) 3223, 2930, 1600 $cm^{-1}$; $^1H$ NMR (400 MHz, $CDCl_3$, 330 K) δ 7.24 (s, 2H), 7.09 (s, 2H), 6.32 (br s, 2H), 5.50 (br s, 2H), 4.02 (s, 6H), 4.00 (br s, 2H), 3.97 (s, 6H), 2.38-2.28 (m, 2H), 1.90-1.80 (m, 2H), 1.55-1.35 (m, 4H); $^{13}C$ NMR (100 MHz, $CDCl_3$, 330 K) ppm 156.2, 153.2, 147.1, 145.3, 141.0, 115.7, 109.2, 106.6, 103.6, 56.2 (2C), 56.1, 33.0, 24.9; HRMS (CI): Exact mass calcd for $C_{28}H_{31}Cl_2N_4O_4[M+H]^+$ 557.1717. found 557.1717.

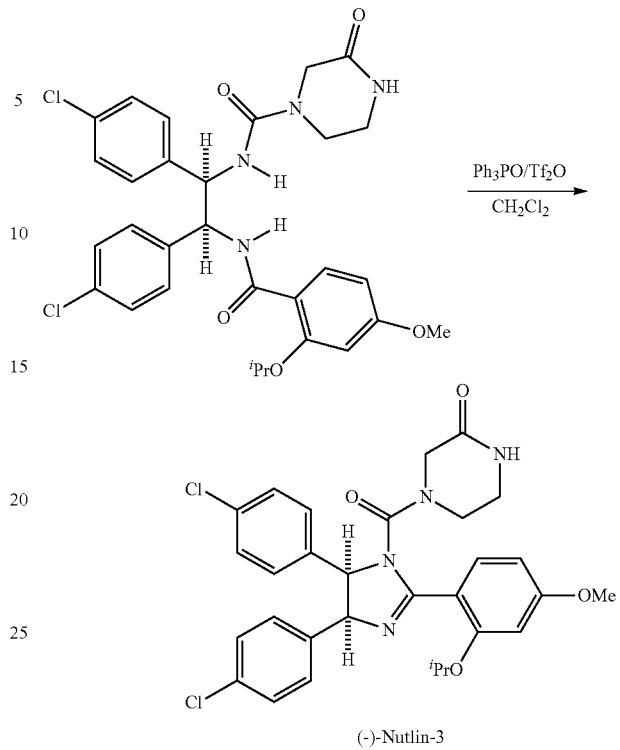

(−)-NUTLIN-3 (1). See Pemberton et al., 2008, which is incorporated herein by reference. Tf$_2$O (28.1 μL, 166.8 μmol) was added to a stirred solution of Ph$_3$PO (92.8 mg, 333.6 μmol) in $CH_2Cl_2$ (500 μL) at 0° C. The mixture was stirred for 10 min before the urea (50.0 mg, 83.4 μmol) was added as a solution in $CH_2Cl_2$ (600 μL), and the reaction was stirred for 1 h at 0° C. The reaction mixture was allowed to warm to room temperature before addition of aq. NaHCO$_3$. The organic layer was separated, the aqueous layer was extracted with $CH_2Cl_2$, and the combined organic layers were then dried over MgSO$_4$, filtered, and concentrated. Column chromatography (0-4% methanol in dichloromethane) of the residue provided the compound as a white solid (42.5 mg, 88%). Mp 127.0-129.0° C.; $[\alpha]_D^{20}$ −150 (c 0.13, $CHCl_3$); $R_f$=0.24 (5% MeOH/$CH_2Cl_2$); IR (film) 3229, 2980, 2935, 2247, 1678, 1608 $cm^{-1}$; $^1H$ NMR (400 MHz, $CDCl_3$) δ 7.59 (d, J=8.8 Hz, 1H), 7.08 (d, J=8.4 Hz, 2H), 7.02 (d, J=8.0 Hz, 2H), 6.92 (d, J=8.4 Hz, 2H), 6.86 (d, J=8.4 Hz, 2H), 6.66 (s, 1H), 6.54 (dd, J=8.4, 1.6 Hz, 1H), 6.47 (br s, 1H), 5.55 (d, J=9.6 Hz, 1H), 5.47 (d, J=9.6 Hz, 1H), 4.60 (qq, J=6.0, 6.0 Hz, 1H), 3.83 (s, 3H), 3.75 (d, J=18.0 Hz, 1H), 3.62 (d, J=18.0 Hz, 1H), 3.40-3.31 (m, 1H), 3.23-3.13 (m, 1H), 2.97 (br s, 2H), 1.37 (d, J=6.0 Hz, 3H), 1.32 (d, J=6.0 Hz, 3H); $^{13}C$ NMR (100 MHz, $CDCl_3$) ppm 166.9, 163.0, 160.2, 157.0, 154.7, 136.0, 135.0, 133.1, 132.8, 132.1, 129.2, 128.4, 128.1, 127.9, 113.4, 104.6, 100.1, 71.7, 70.9, 69.1, 55.5, 49.4, 41.8, 40.3, 20.03, 20.01; HRMS (CI): Exact mass calcd for $C_{30}H_{31}Cl_2N_4O_4$ $[M+H]^+$ 581.1717. found 581.1705.

This enantiomer corresponded to "enantiomer-a" using the HPLC conditions as described previously in Wang et al., 2007, which is incorporated herein by reference. The compound was found to be 99% ee; (Chiralcel OD, 30% iPrOH/hexanes, 1 mL/min, t$_r$(major)=8.6 min, t$_r$(minor)=not observed). Additionally, the (+)-enantiomer was prepared using an identical procedure with (S,S)—H,$^4$Pyrrolidine-Quin-BAM to form compound 7 (84% ee), which was converted to (+)-Nutlin-3. This compound correlated with "enantiomer-b". and was found to be 85% ee; (Chiralcel OD, 30% iPrOH/hexanes, 1 mL/min, t$_r$(major)=10.5 min, t$_r$(minor)= 8.6 min).

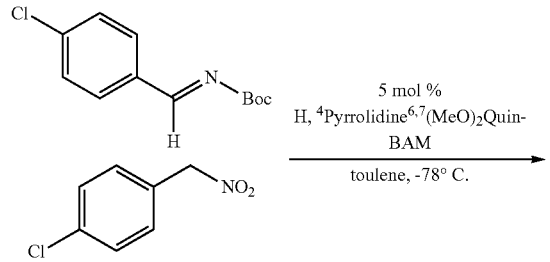

TERT-BUTYL (1R,2S)-1,2-BIS(4-CHLOROPHENYL)-2-NITROETHYL-CARBAMATE. Imine (24.0 mg, 100 μmol) and H,[4]Pyrrolidine[6,7](MeO)$_2$Quin-BAM (3.1 mg, 5.0 μmol) were dispensed into a vial equipped with stir bar. Toluene (1.0 mL) was added and the mixture was chilled to −78° C. before addition of the nitroalkane 9 (18.9 mg, 110 μmol). The reaction was stirred at −78° C. for 24 h. The reaction was kept at the reaction temperature and filtered directly through a pad of silica gel with CH$_2$Cl$_2$. Purification by column chromatography (7-25% ethyl acetate in hexanes) yielded a white solid (39.8 mg, 97%) that was 13:1 dr, 91% ee (average of two runs) by chiral HPLC; (Chiralcel AD-H, 12% $^i$PrOH/hexanes, 1 mL/min, t$_r$(anti, major)=30.5 min, t$_r$(anti, minor)=12.8 min, t$_r$(syn, major)=14.9 min, t$_r$(syn, minor)= 45.6 min). Mp 172.0-174.0° C.; [α]$_D^{20}$ −150 (c 0.13, CHCl$_3$); R$_f$=0.24 (20% EtOAc/hexanes); IR (film) 3381, 2982, 1682, 1551, 1521 cm$^{-1}$; $^1$H NMR (400 MHz, CDCl$_3$) δ 7.50 (d, J=8.4 Hz, 2H), 7.40 (d, J=8.4 Hz, 2H), 7.35 (d, J=8.4 Hz, 2H), 7.28 (d, J=8.8 Hz, 2H), 5.76 (d, J=9.6 Hz, 1H), 5.58 (dd, J=9.6, 9.6 Hz, 1H), 4.78 (d, J=9.6 Hz, 1H), 1.28 (s, 9H); $^{13}$C NMR (150 MHz, CDCl$_3$) ppm 154.2, 136.6, 135.6, 134.9, 130.1, 129.7, 129.3, 129.1, 128.6, 93.2, 80.8, 56.1, 28.0; HRMS (CI): Exact mass calcd for C$_{19}$H$_{21}$Cl$_2$N$_2$O$_4$ [M+H]$^+$ 411.0873. found 411.0865.

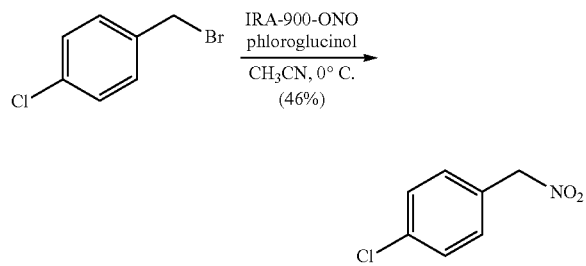

1-CHLORO-4-(NITROMETHYL)BENZENE. 4-Chlorobenzyl bromide (3.000 g, 14.60 mmol) and phloroglucinol (1.841 g, 14.60 mmol) were dissolved in CH$_3$CN (32.3 mL) in a round bottom flask at room temperature. The reaction mixture was then chilled to 0° C. before IRA900-ONO (12.4 g, 2.4 equiv.) resin was added. The suspension was then stirred at 0° C. for 70 min and filtered. The resin was rinsed thoroughly with diethyl ether. The filtrate and rinsate were combined and concentrated. Column chromatography of the residue (0-3% ethyl acetate in hexanes) afforded a crystalline solid (1.1642 g, 46%). Mp 28.0-29.0° C.; R$_f$=0.45 (20% EtOAc/hexanes); IR (film) 3095, 3036, 2916, 1555 cm$^{-1}$; $^1$H NMR (400 MHz, CDCl$_3$) δ 7.45-7.35 (m, 4H), 5.41 (s, 2H); $^{13}$C NMR (100 MHz, CDCl$_3$) ppm 136.3, 131.4, 129.4, 128.0, 79.1; HRMS (CI): Exact mass calcd for C$_7$H$_7$ClNO$_2$ [M+H]$^+$ 172.0160. found 172.0157.

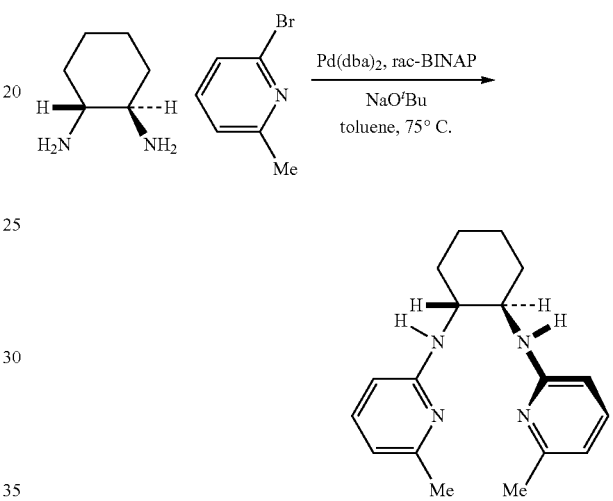

H,[6]ME-BAM. Pd(dba)$_2$ (10.1 mg, 17.5 μmol), rac-BINAP (21.8 mg, 35.0 μmol), and sodium tert-butoxide (286.4 mg, 2.98 mmol) were loaded into a round bottom flask in a glove box. Toluene (10 mL, 0.10M) was added to the mixture, followed by (R,R)-diaminocyclohexane (100.0 mg, 876.0 μmol). 2-Bromo-6-methylpyridine (301.5 mg, 1.75 mmol) was added as a solution in toluene. The reaction was allowed to stir at 80° C. and monitored by TLC. The reaction was then cooled to room temperature, concentrated, and purified by flash column chromatography on silica gel (5% triethylamine, 10% ethyl acetate in hexanes) affording a white solid (200 mg, 77%). [α]$_D^{20}$ +110 (c 0.10, CHCl$_3$); mp 126-128° C.; R$_f$=0.17 (5% Et$_3$N, 10% EtOAc/hexanes); IR (neat) 3256, 3051, 2927, 2855, 1559 cm$^{-1}$; $^1$H NMR (400 MHz, CDCl$_3$) δ 7.19 (dd, J=8.0, 8.0 Hz, 2H), 6.35 (d, J=7.2 Hz, 2H), 6.11 (d, J=8.4 Hz, 2H), 5.16 (br s, 2H), 3.73-3.64 (m, 2H), 2.37 (s, 6H), 2.27-2.18 (m, 2H), 1.78-1.65 (m, 2H), 1.50-1.28 (m, 4H); $^{13}$C NMR (100 MHz, CDCl$_3$) ppm 158.2, 156.5, 137.3, 111.3, 104.2, 55.0, 32.1, 24.4, 24.3; HRMS (EI) Exact mass calcd for C$_{18}$H$_{24}$N$_4$ [M]$^+$ 296.2001. found 296.1994.

H,[4]PYRROLIDINEQUIN-BAM.HOTF. To a flame-dried vial with stir bar was added H,[4]PYRROLIDINEQUIN-BAM (286.3 MG, 565.1 μmol) and dichloromethane (2 mL). Trifluoromethanesulfonic acid (50.0 μL, 565 μmol) was added dropwise to the stirring solution at room temperature. The reaction mixture was allowed to stir an additional 10 minutes before concentration to a light brown solid that was used without further purification. Other catalyst acid salts were made in a similar fashion.

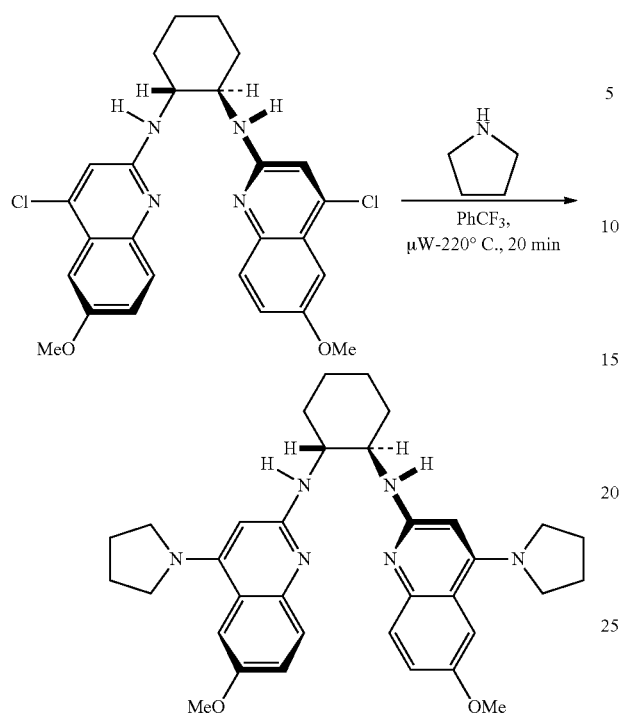

H,[4]PYRROLIDINE[6]MEOQUIN-BAM. A 2-5 mL microwave vial was charged with H,[4]Cl[6]OMeQuin-BAM (200 mg, 402 μmol), pyrrolidine (660 μL, 8.041 mmol), and trifluoromethylbenzene (2 mL). This suspension was heated at 220° C. and stirred in the microwave for 20 min. The reaction was then concentrated and purified by column chromatography (5-10% methanol in dichloromethane) to provide a light brown solid. This material was dissolved in dichloromethane and then washed with 3 M aq NaOH. The combined organic layers were dried over MgSO$_4$ and concentrated to afford a light brown powder (174.4 mg, 77%); $[\alpha]_D^{20}$ +350 (c 0.14, CHCl$_3$); R$_f$=0.29 (10% MeOH/CH$_2$Cl$_2$); IR (film) 3261, 2930, 2856, 1595, 1531 cm$^{-1}$; $^1$H NMR (400 MHz, CDCl$_3$) δ 7.61 (d, J=9.2 Hz, 2H), 7.27 (d, J=2.8 Hz, 2H), 7.11 (dd, J=8.8, 2.8 Hz, 2H), 5.57 (br s, 2H), 5.35 (s, 2H), 4.03 (br s, 2H), 3.82 (s, 6H), 3.32-3.20 (m, 4H), 3.15-3.05 (m, 4H), 2.32-2.25 (m, 2H), 1.90-1.75 (m, 10H), 1.50-1.30 (m, 4H); $^{13}$C NMR (100 MHz, CDCl$_3$) ppm 157.3, 153.0, 152.8, 144.8, 127.5, 118.9, 118.4, 106.0, 94.0, 56.4, 55.6, 51.4, 33.4, 25.4, 25.1; HRMS (ESI): Exact mass calcd for C$_{34}$H$_{43}$N$_6$O$_2$ [M+H]$^+$ 567.3448. found 567.3442.

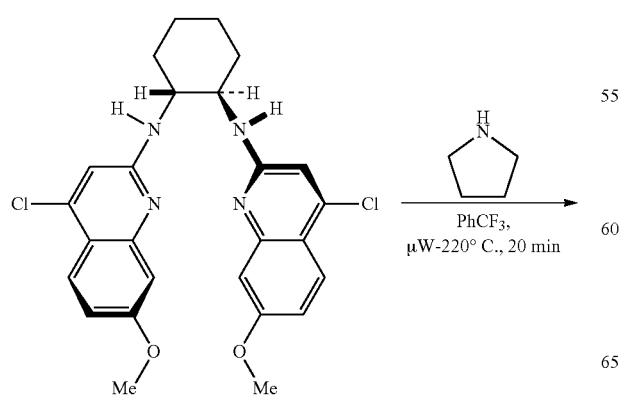

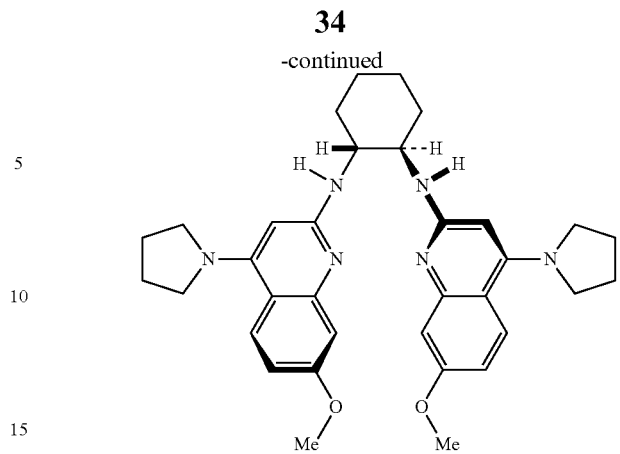

H,[4]PYRROLIDINE[7]MEOQUIN-BAM. A 2-5 mL microwave vial was charged with H,[4]Cl[7]MeOQuin-BAM (200 mg, 402 μmol), pyrrolidine (660 μL, 8.041 mmol), and trifluoromethylbenzene (2 mL). This suspension was heated at 220° C. and stirred in the microwave for 20 min. The reaction was then concentrated and purified by column chromatography (5-10% methanol in dichloromethane) to provide a light brown solid. This material was dissolved in dichloromethane and then washed with 3 M aq NaOH. The combined organic layers were dried over MgSO$_4$ and concentrated to afford a light brown powder (123.5 mg, 54%); $[\alpha]_D^{20}$ +480 (c 0.13, CHCl$_3$); R$_f$=0.39 (10% MeOH/CH$_2$Cl$_2$); IR (film) 3253, 2930, 2855, 1616, 1589, 1526 cm$^{-1}$; $^1$H NMR (500 MHz, CDCl$_3$) δ 7.76 (d, J=9.0 Hz, 2H), 7.09 (s, 2H), 6.65 (dd, J=9.5, 2.5 Hz, 2H), 5.77 (br s, 2H), 5.23 (s, 2H), 4.04 (br s, 2H), 3.88 (s, 6H), 3.35-3.25 (m, 4H), 3.20-3.10 (m, 4H), 2.33-2.25 (m, 2H), 1.90-1.78 (m, 10H), 1.55-1.35 (m, 4H); $^{13}$C NMR (125 MHz, CDCl$_3$) ppm 159.9, 158.6, 153.2, 151.5, 125.9, 112.7, 110.4, 105.8, 90.7, 56.3, 55.2, 51.5, 33.3, 25.6, 25.0; HRMS (ESI): Exact mass calcd for C$_{34}$H$_{43}$N$_6$O$_2$ [M+H]$^+$ 567.3447. found 567.3467.

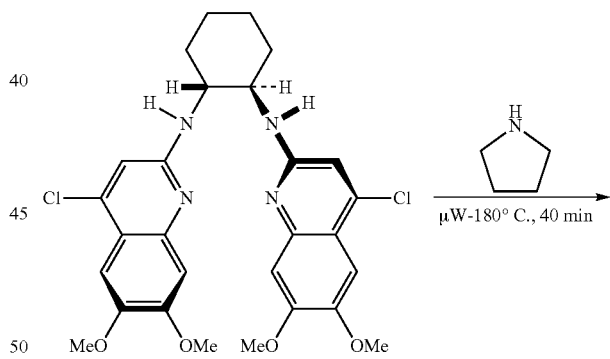

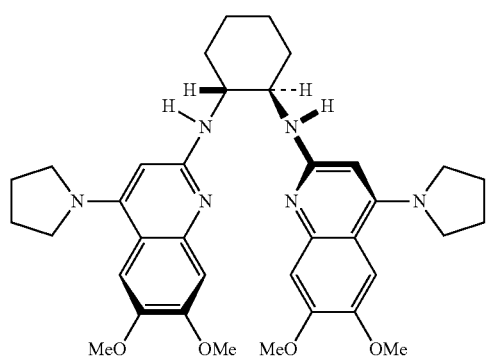

H,[4]PYRROLIDINE[6,7](MEO)$_2$QUIN-BAM. A 2-5 mL microwave vial was charged with [4]Cl[6,7](MeO)$_2$Quin-BAM (1.000 g, 1.794 mmol) and pyrrolidine (2.9 mL, 36 mmol). This suspension was heated at 180° C. and stirred in the microwave for 40 min. The reaction was then concentrated and purified by column chromatography (2-5-10% methanol in dichloromethane with 1% AcOH) to provide a light brown solid. This material was dissolved in dichloromethane and then washed with 3 M aq NaOH. The combined organic layers were dried over MgSO$_4$ and concentrated. The material was then triturated with hexanes to afford a light brown viscous foam (351.1 mg, 31%); [α]$_D^{20}$ +340 (c 0.11, CHCl$_3$); R$_f$=0.22 (10% MeOH/1% AcOH/CH$_2$Cl$_2$); IR (film) 3391, 2931, 2855, 1593 cm$^{-1}$; $^1$H NMR (400 MHz, CDCl$_3$) δ 7.24 (s, 2H), 7.10 (s, 2H), 5.51 (br s, 2H), 5.37 (s, 2H), 3.99 (br s, 2H), 3.99 (s, 6H), 3.89 (s, 6H), 3.37-3.26 (m, 4H), 3.23-3.13 (m, 4H), 2.35-2.25 (m, 2H), 1.91-1.79 (m, 10H), 1.52-1.38 (m, 4H); $^{13}$C NMR (100 MHz, CDCl$_3$) ppm 157.6, 152.8, 150.7, 146.0, 143.5, 111.7, 106.5, 105.2, 91.9, 56.3, 55.8, 55.5, 51.2, 33.3, 25.3, 25.0; HRMS (CI): Exact mass calcd for C$_{36}$H$_{47}$N$_6$O$_4$ [M+H]$^+$ 627.3653. found 627.3658.

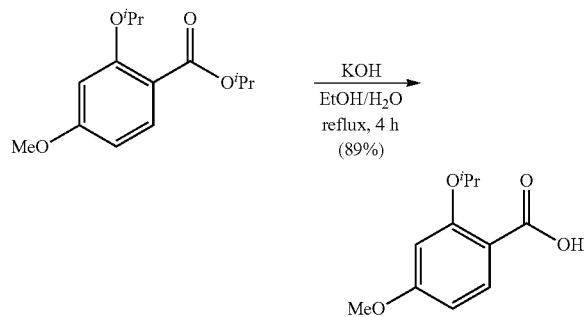

2-ISOPROPOXY-4-METHOXYBENZOIC ACID. See Hattori et al., 2003., which is incorporated by reference herein. Ester (985.0 mg, 3.904 mmol) was boiled with KOH (703.8 mg, 12.54 mmol) in a mixture of ethanol (11.7 mL) and water (2.3 mL) for 4 h. EtOH was then removed by evaporation. The remaining material was diluted with water and treated with 3 M HCl until precipitation occurred. The suspension was then extracted with diethyl ether. The combined organic layers were washed with brine before drying over MgSO$_4$. The solution was concentrated to a red oil (733.2 mg, 89%) that was pure by $^1$H NMR. R$_f$=0.33 (50% EtOAc/hexanes); IR (film) 3261, 2981, 1730, 1608 cm$^{-1}$; $^1$H NMR (500 MHz, CDCl$_3$) δ 10.91 (br s, 1H), 8.12 (d, J=9.0 Hz, 1H), 6.62 (dd, J=9.0, 2.5 Hz, 1H), 6.52 (d, J=2.0 Hz, 1H), 4.81 (heptet, J=6.5 Hz, 1H), 3.86 (s, 3H), 1.47 (d, J=6.0 Hz, 6H); $^{13}$C NMR (100 MHz, CDCl$_3$) ppm 165.5, 164.9, 157.8, 135.4, 111.4, 106.8, 100.7, 73.9, 55.7, 21.9; HRMS (ESI): Exact mass calcd for C$_{11}$H$_{14}$NaO$_4$ [M+Na]$^+$ 233.0790. found 233.0795.

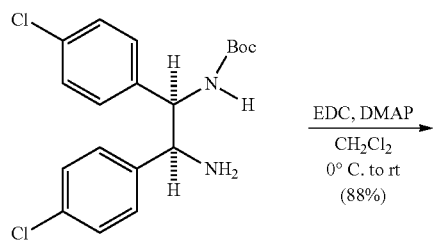

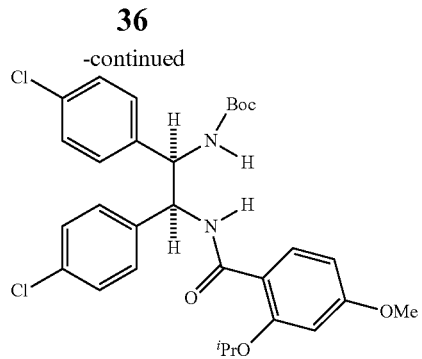

TERT-BUTYL (1R,2S)-1,2-BIS(4-CHLOROPHENYL)-2-(2-ISOPROPOXY-4-METHOXYBENZAMIDO)ETH-YLCARBAMATE. The amine (170.0 mg, 445.8 μmol) and carboxylic acid (93.7 mg, 445.8 μmol) were dissolved in CH$_2$Cl$_2$ (2.2 mL) at room temperature. The solution was chilled to 0° C. and EDC (111.1 mg, 579.6 μmol) and DMAP (5.4 mg, 44.6 μmol) were added. The reaction mixture was stirred and allowed to gradually warm to room temperature. After 16 h, the reaction mixture was diluted with water and extracted with CH$_2$Cl$_2$. The combined organic layers were washed once with water, dried over MgSO$_4$, and concentrated. The resulting white solid was washed with CH$_2$Cl$_2$ and hexanes, leaving a white solid (224.5 mg, 88%) that was pure by NMR. Mp 239.0-241.0° C. (decomp.); [α]$_D^{20}$ −29 (c 0.13, CHCl$_3$); R$_f$=0.13 (20% EtOAc/hexanes); IR (film) 3355, 2976, 1680, 1629, 1607, 1529 cm$^{-1}$; $^1$H NMR (400 MHz, CDCl$_3$) δ 8.39 (d, J=7.2 Hz, 1H), 8.19 (d, J=8.8 Hz, 1H), 7.26 (d, J=8.4 Hz, 2H), 7.21 (d, J=8.4 Hz, 2H), 7.02 (d, J=6.8 Hz, 2H), 6.93 (d, J=8.4 Hz, 2H), 6.59 (dd, J=8.8, 2.4 Hz, 1H), 6.46 (d, J=1.6 Hz, 1H), 5.91 (br s, 1H), 5.78 (br s, 1H), 5.07 (br s, 1H), 4.75-4.60 (m, 1H), 3.84 (s, 3H), 1.38 (s, 9H), 1.30-1.21 (m, 6H); $^{13}$C NMR (100 MHz, CDCl$_3$) ppm 165.6, 163.6, 157.2, 155.0, 136.9, 136.7, 134.2, 133.6, 133.3, 128.6 (2C), 128.5, 128.3, 114.1, 105.2, 100.2, 79.9, 71.4, 59.5, 56.6, 55.5, 28.3, 22.0, 21.6; HRMS (ESI): Exact mass calcd for C$_{30}$H$_{34}$Cl$_2$N$_2$NaO$_5$ [M+Na]$^+$ 595.1742. found 595.1743.

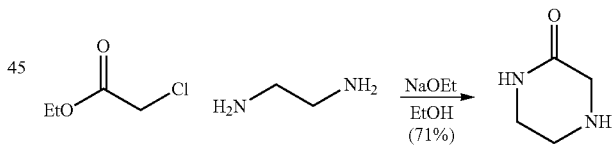

2-OXO-PIPERAZINE. See U.S. Pat. No. 6,835,371, which is incorporated by reference herein. The resulting orange oil was purified by column chromatography (10% MeOH in CH$_2$Cl$_2$ w/1% NH$_4$OH). A yellow solid (2.8634 g, 71%) was obtained that was sufficiently pure by $^1$H NMR. R$_f$=0.07 (10% MeOH/CH$_2$Cl$_2$ w/1% NH$_4$OH); IR (film) 3400, 1650 cm$^{-1}$; $^1$H NMR (500 MHz, CDCl$_3$) δ 7.18 (br s, 1H), 3.46 (s, 2H), 3.35-3.28 (m, 2H), 2.98 (t, J=5.5 Hz, 2H), 1.89 (br s, 1H); $^{13}$C NMR (125 MHz, CDCl$_3$) ppm 170.4, 49.6, 42.7, 42.2; HRMS (CI): Exact mass calcd for C$_4$H$_9$N$_2$O [M+H]$^+$ 101.0709. found 101.0714.

Example 3

Synthesis of [8]MeOPBAM

[4]Cl[8]MeOQuinBAM. A 100 mL round bottom flask was charged with Pd(dba)$_2$ (25.2 mg, 43.8 μmol), rac-BINAP (27.3 mg, 43.8 µmol), sodium tert-butoxide (632.0 mg, 6.576 mmol), (R,R)-diaminocyclohexane (250.3 mg, 2.192 mmol), and the quinoline (1.0000 g, 4.385 mmol).[1] Toluene (22 mL) was added, and the reaction mixture was heated at 70° C. and stirred for 3.5 h. The reaction was cooled to room temperature, diluted with $CH_2Cl_2$, and filtered through celite. The filtrate was concentrated and purified by column chromatography (25-50% ethyl acetate in hexanes) to provide a yellow solid (642.6 mg, 62%). $[\alpha]_D^{20}$ +530 (c 0.16, $CHCl_3$); $R_f$=0.31 (50% EtOAc/hexanes); IR (film) 3240, 2933, 1607, 1545 cm$^{-1}$; $^1$H NMR (400 MHz, $CDCl_3$) δ 7.54 (dd, J=8.4, 0.8 Hz, 2H), 7.17 (dd, J=7.6, 0.8 Hz, 2H), 7.01 (dd, J=7.6, 0.8 Hz, 2H), 6.59 (s, 2H), 6.38 (br s, 2H), 4.15-3.95 (m, 2H), 4.04 (s, 6H), 2.45-2.30 (m, 2H), 1.85-1.70 (m, 2H), 1.50-1.30 (m, 4H); $^{13}$C NMR (150 MHz, $CDCl_3$) ppm 155.9, 153.2, 142.1, 140.0, 122.2, 121.9, 116.2, 112.7, 109.8, 56.6, 56.2, 32.5, 24.7; HRMS (ESI): Exact mass calcd for $C_{26}H_{27}Cl_2N_4O_2$ [M+H]$^+$ 497.1511. found 497.1521.

[1] Adapted from Wagaw, S.; Rennels, R.; Buchwald, S. *J Am. Chem. Soc.* 1997, 119, 8451-8458.

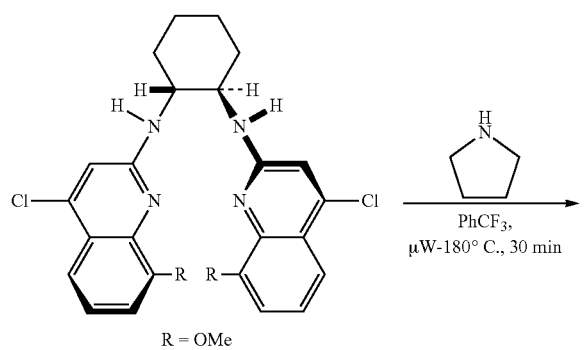

R = OMe $^8$MeOPBAM. A 0.5-2.0 mL microwave vial was charged with the corresponding $^4$ClBAM (200.0 mg, 402.1 µmol), pyrrolidine (132 µL, 1.61 mmol), and trifluoromethylbenzene (1.2 mL). This suspension was heated at 180° C. and stirred in the microwave for 30 min. The reaction mixture was purified by column chromatography (2-5% methanol in dichloromethane with 0.5% AcOH) to provide a light brown solid. This material was dissolved in dichloromethane and then washed with 3 M aq NaOH. The combined organic layers were dried over $MgSO_4$ and concentrated. The resulting solid was dissolved in EtOAc and washed with water, dried over $MgSO_4$, filtered, and concentrated to a light brown solid (108.4 mg, 48%). $[\alpha]_D^{20}$ +320 (c 0.14, $CHCl_3$); $R_f$=0.24 (10% MeOH/$CH_2Cl_2$); IR (film) 3244, 2933, 2857, 1637, 1593 cm$^{-1}$; $^1$H NMR (400 MHz, $CDCl_3$) δ 7.49 (d, J=8.4 Hz, 2H), 6.93 (dd, J=7.6, 7.6 Hz, 2H), 6.88 (d, J=7.2 Hz, 2H), 5.78 (br s, 2H), 5.52 (br s, 2H), 4.10-4.00 (m, 2H), 4.00 (s, 6H), 3.41-3.29 (m, 4H), 3.28-3.15 (m, 4H), 2.40-2.27 (m, 2H), 1.90-1.73 (m, 8H), 1.73-1.65 (m, 2H), 1.60-1.40 (m, 4H); $^{13}$C NMR (150 MHz, $CDCl_3$, 325 K) ppm 157.5, 153.8, 153.7, 141.6, 119.5, 118.5, 117.3, 109.0, 93.3, 56.5, 56.3, 51.7, 33.1, 25.4, 24.9; HRMS (ESI): Exact mass calcd for $C_{34}H_{43}N_6O_2$ [M+H]$^+$ 567.3448. found 567.3431.

Example 4

Larger Scale Synthesis of $^8$MeOPBAM

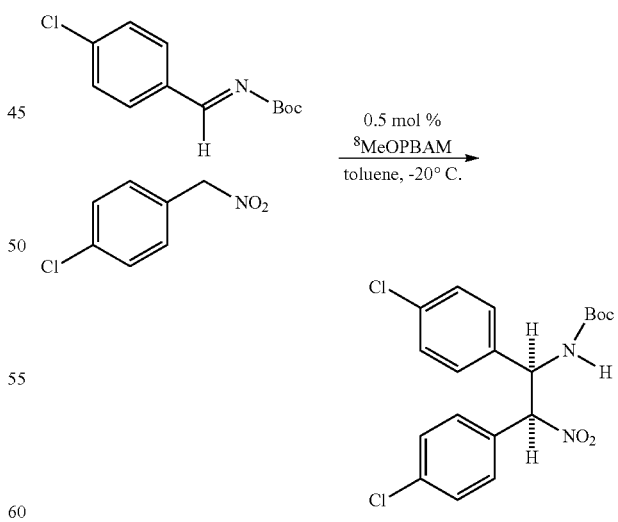

1-Chloro-4-(nitromethyl)benzene. $NaNO_2$ (7.600 g, 109.5 mmol), urea (8.800 g, 146.0 mmol), and phloroglucinol (10.100 g, 80.30 mmol) were stirred with DMF (111 mL) at room temperature until homogenous. The reaction mixture was chilled to –20° C. before the addition of bromide (15.0 g, 73.0 mmol). The mixture was stirred at –20° C. for 3.25 h before pouring into ice water. The mixture was extracted with ether. The combined organic extracts were washed with water, dried over $MgSO_4$, filtered, and concentrated. Column chromatography (0-4% EtOAc/hexanes) provided a clear oil that froze/solidified to a slightly yellow crystalline solid upon storage in a freezer (13.1 g, 45%). Mp 28.0-29.0° C.; $R_f$=0.45 (20% EtOAc/hexanes); IR (film) 3095, 3036, 2916, 1555 cm$^{-1}$; $^1$H NMR (400 MHz, $CDCl_3$) δ 7.45-7.35 (m, 4H), 5.41 (s, 2H); $^{13}$C NMR (100 MHz, $CDCl_3$) ppm 136.3, 131.4, 129.4, 128.0, 79.1; HRMS (CI): Exact mass calcd for $C_7H_7ClNO_2$ [M+H]$^+$ 172.0160. found 172.0157.

tert-Butyl (1R,2S)-1,2-bis(4-chlorophenyl)-2-nitroethylcarbamate. Imine (1.5000 g, 6.2580 mmol) and $^8$MeOPBAM (196.1 mg, 312.9 µmol) were dispensed into a 100 mL round bottom flask equipped with stir bar. Toluene (63 mL) was added and the mixture was chilled to –78° C. before addition of the nitroalkane 9 (1.1810 g, 6.8840 mmol). The reaction was stirred at −78° C. for 24 h. The reaction was kept at the reaction temperature and filtered directly through a pad of silica gel with $CH_2Cl_2$. The filtrate was concentrated to give 2.2772 g of a white solid that was 6:1 anti:syn. A portion (1.1000 g) of this material was recrystallized from toluene to provide colorless crystals. The crystalline material (586.8 mg) was separated from the mother liquor and found to be >200:1 dr, 97% ee by chiral HPLC; (Chiralcel AD-H, 12% $^i$PrOH/hexanes, 1 mL/min, $t_r$(anti, major)=30.5 min, $t_r$(anti, minor)=12.8 min, $t_r$(syn, major)=14.9 min, $t_r$(syn, minor)= 45.6 min). Mp 172.0-174.0° C.; $[\alpha]_D^{20}$ −150 (c 0.13, $CHCl_3$); $R_f$=0.24 (20% EtOAc/hexanes); IR (film) 3381, 2982, 1682, 1551, 1521 cm$^{-1}$; $^1$H NMR (400 MHz, $CDCl_3$) δ 7.50 (d, J=8.4 Hz, 2H), 7.40 (d, J=8.4 Hz, 2H), 7.35 (d, J=8.4 Hz, 2H), 7.28 (d, J=8.8 Hz, 2H), 5.76 (d, J=9.6 Hz, 1H), 5.58 (dd, J=9.6, 9.6 Hz, 1H), 4.78 (d, J=9.6 Hz, 1H), 1.28 (s, 9H); $^{13}$C NMR (150 MHz, $CDCl_3$) ppm 154.2, 136.6, 135.6, 134.9, 130.1, 129.7, 129.3, 129.1, 128.6, 93.2, 80.8, 56.1, 28.0; HRMS (CI): Exact mass calcd for $C_{19}H_{21}Cl_2N_2O_4$ [M+H]$^+$ 411.0873. found 411.0865.

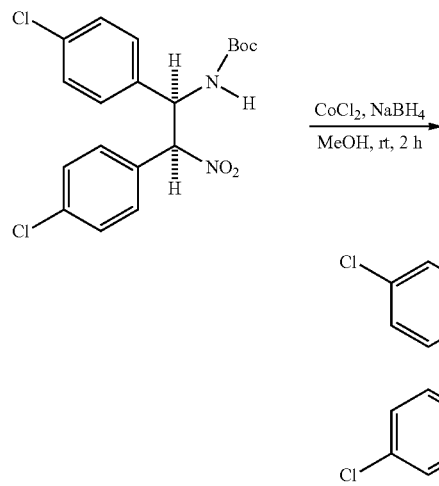

tert-butyl (1R,2S)-2-amino-1,2-bis(4-chlorophenyl)ethyl-carbamate. The nitroalkane (2.9105 g, 7.067 mmol) was dissolved in MeOH (50 mL) at room temperature. $CoCl_2$ (918.8 mg, 7.067 mmol) was added and the reaction mixture was chilled to 0° C. before $NaBH_4$ (1.337 g, 35.33 mmol) was added in three portions over 30 min. The reaction mixture was stirred at 0° C. for an additional 30 min before the mixture was quenched with sat. aq. $NH_4Cl$. The reaction mixture was adjusted to pH 10 with conc. aq. $NH_4OH$. The suspension was filtered and solid on filter was washed with water. Solid was subsequently washed with $CH_2Cl_2$. $CH_2Cl_2$ wash was dried over $MgSO_4$, filtered, and concentrated to afford the product as a white/gray solid (2.2423 g, 83%). Mp 149.0-150.0° C.; $[\alpha]_D^{20}$ +67 (c 0.12, $CHCl_3$); $R_f$=0.12 (50% EtOAc/hexanes); IR (film) 3377, 2981, 1683, 1523 cm$^{-1}$; $^1$H NMR (400 MHz, $CDCl_3$) δ 7.24 (d, J=8.4 Hz, 2H), 7.21 (d, J=8.4 Hz, 2H), 7.00 (d, J=8.4 Hz, 2H), 6.93 (d, J=8.4 Hz, 2H), 5.49 (d, J=7.6 Hz, 1H), 4.79 (br s, 1H), 4.23 (br s, 1H), 1.50 (s, 2H), 1.36 (s, 9H); $^{13}$C NMR (100 MHz, $CDCl_3$) ppm 155.0, 140.3 (2C), 133.3, 133.2, 128.7, 128.4, 128.2 (2C), 79.8, 59.5, 59.1, 28.2; HRMS (ESI): Exact mass calcd for $C_{19}H_{23}Cl_2N_2O_2$ [M+H]$^+$ 381.1137. found 381.1147.

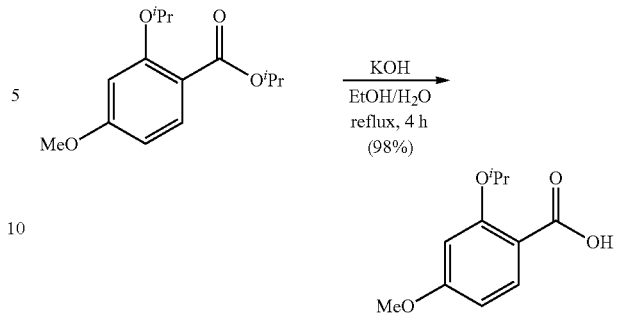

2-isopropoxy-4-methoxybenzoic acid. Ester (2.8518 g, 11.30 mmol) was boiled with KOH (1.9023 g, 33.91 mmol) in a mixture of ethanol (31 mL) and water (6 mL) for 3 h. EtOH was then removed by evaporation. The remaining material was diluted with water and treated with 3 M HCl until precipitation occurred. The suspension was then extracted with diethyl ether. The combined organic layers were washed with brine before drying over $MgSO_4$. The solution was concentrated to a red oil (2.3342 g, 98%) that was pure by $^1$H NMR. $R_f$=0.33 (50% EtOAc/hexanes); IR (film) 3261, 2981, 1730, 1608 cm$^{-1}$; $^1$H NMR (500 MHz, $CDCl_3$) δ 10.91 (br s, 1H), 8.12 (d, J=9.0 Hz, 1H), 6.62 (dd, J=9.0, 2.5 Hz, 1H), 6.52 (d, J=2.0 Hz, 1H), 4.81 (heptet, J=6.5 Hz, 1H), 3.86 (s, 3H), 1.47 (d, J=6.0 Hz, 6H); $^{13}$C NMR (100 MHz, $CDCl_3$) ppm 165.5, 164.9, 157.8, 135.4, 111.4, 106.8, 100.7, 73.9, 55.7, 21.9; HRMS (ESI): Exact mass calcd for $C_{11}H_{14}NaO_4$ [M+Na]$^+$ 233.0790. found 233.0795.

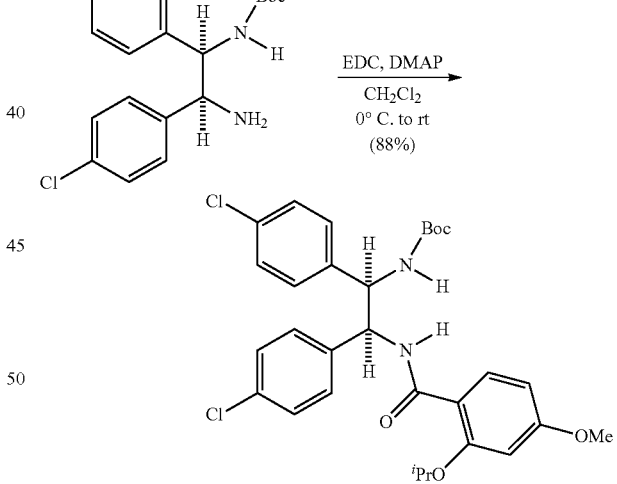

tert-Butyl (1R,2S)-1,2-bis(4-chlorophenyl)-2-(2-isopropoxy-4-methoxybenz-amido)ethylcarbamate. The amine (1.5 g, 3.934 mmol) and carboxylic acid (826.9 mg, 3.934 mmol) were dissolved in $CH_2Cl_2$ (20 mL) at room temperature. The solution was chilled to 0° C. and EDC.HCl (1.131 g, 5.901 mmol) and DMAP (48.0 mg, 393.4 μmol) were added. The reaction mixture was allowed to gradually warm to room temperature while stirring. After 16 h, the reaction mixture was diluted with $CH_2Cl_2$, stirred for one hour, and washed with water. The organic layer was washed with water, dried over $MgSO_4$, and concentrated. The resulting white solid was washed with $CH_2Cl_2$ and hexanes, leaving a white solid (2.256 g, 75%). Mp 239.0-241.0° C. (decomp.); $[\alpha]_D^{20}$ −29 (c 0.13, CHCl$_3$); $R_f$=0.13 (20% EtOAc/hexanes); IR (film) 3355, 2976, 1680, 1629, 1607, 1529 cm$^{-1}$; $^1$H NMR (400 MHz, CDCl$_3$) δ 8.39 (d, J=7.2 Hz, 1H), 8.19 (d, J=8.8 Hz, 1H), 7.26 (d, J=8.4 Hz, 2H), 7.21 (d, J=8.4 Hz, 2H), 7.02 (d, J=6.8 Hz, 2H), 6.93 (d, J=8.4 Hz, 2H), 6.59 (dd, J=8.8, 2.4 Hz, 1H), 6.46 (d, J=1.6 Hz, 1H), 5.91 (br s, 1H), 5.78 (br s, 1H), 5.07 (br s, 1H), 4.75-4.60 (m, 1H), 3.84 (s, 3H), 1.38 (s, 9H), 1.30-1.21 (m, 6H); $^{13}$C NMR (100 MHz, CDCl$_3$) ppm 165.6, 163.6, 157.2, 155.0, 136.9, 136.7, 134.2, 133.6, 133.3, 128.6 (2C), 128.5, 128.3, 114.1, 105.2, 100.2, 79.9, 71.4, 59.5, 56.6, 55.5, 28.3, 22.0, 21.6; HRMS (ESI): Exact mass calcd for C$_{30}$H$_{34}$Cl$_2$N$_2$NaO$_5$ [M+Na]$^+$ 595.1742. found 595.1743.

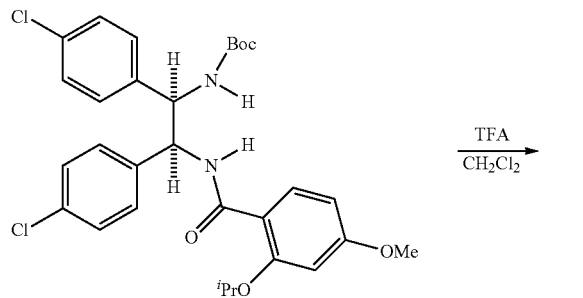

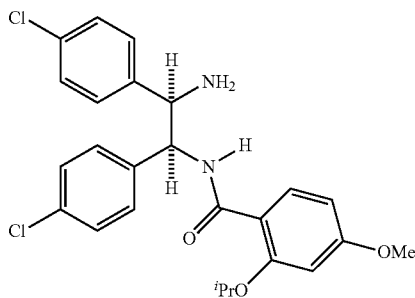

N-((1S,2R)-2-AMINO-1,2-BIS(4-CHLOROPHENYL) ETHYL)-2-ISOPROPOXY-4-METHOXYBENZAMIDE. Amide (1.700 g, 2.964 mmol) was dissolved in CH$_2$Cl$_2$ (30 mL). TFA (8.8 mL, 118.6 mmol) was added and the mixture was stirred at room temperature for 16 h. The reaction mixture was poured into satd. aq. NaHCO$_3$ and extracted with CH$_2$Cl$_2$. The combined organic layers were dried over MgSO$_4$, filtered, and concentrated to a light brown foam (1.3107 g, 93%). $[\alpha]_D^{20}$ −140 (c 0.11, CHCl$_3$); $R_f$=0.46 (10% MeOH/CH$_2$Cl$_2$); IR (film) 3376, 2925, 2853, 1644, 1605, 1521 cm$^{-1}$; $^1$H NMR (400 MHz, CDCl$_3$) δ 8.88 (d, J=8.0 Hz, 1H), 8.13 (d, J=8.8 Hz, 1H), 7.24 (d, J=8.4 Hz, 2H), 7.20 (d, J=8.4 Hz, 2H), 7.03 (d, J=8.4 Hz, 2H), 7.00 (d, J=8.8 Hz, 2H), 6.56 (dd, J=8.8, 2.4 Hz, 1H), 6.49 (d, J=2.0 Hz, 1H), 5.43 (dd, J=8.0, 4.8 Hz, 1H), 4.75 (qq, J=6.0, 6.0 Hz, 1H), 4.41 (d, J=4.8 Hz, 1H), 3.83 (s, 3H), 1.45 (d, J=5.6 Hz, 3H), 1.44 (d, J=5.6 Hz, 3H); $^{13}$C NMR (100 MHz, CDCl$_3$) ppm 164.7, 163.3, 157.2, 140.7, 136.8, 134.1, 133.2, 133.1, 129.1, 128.4, 128.3, 128.2, 115.0, 105.1, 100.3, 71.5, 59.0, 58.6, 55.5, 22.2, 22.0; HRMS (ESI): Exact mass calcd for C$_{25}$H$_{27}$Cl$_2$N$_2$O$_3$ [M+H]$^+$ 473.1399. found 473.1400.

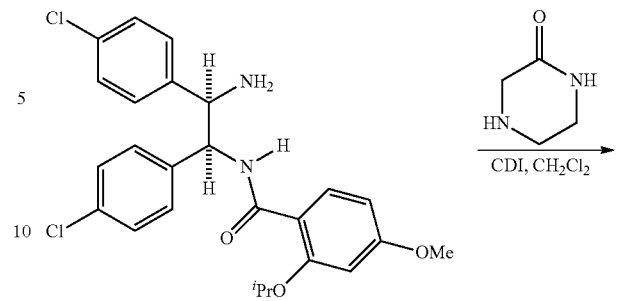

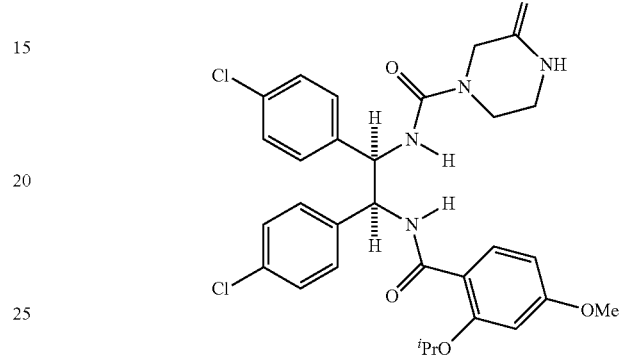

N-((1R,2S)-1,2-Bis(4-chlorophenyl)-2-(2-isopropoxy-4-methoxybenzamido)ethyl)-3-oxopiperazine-1-carboxamide. Amine (1.2 g, 211.2 μmol) was dissolved in CH$_2$Cl$_2$ (13 mL) and stirred at room temperature. CDI (493.1 mg, 3.041 mmol) was added and the reaction was stirred for 1.5 h. 2-Oxo-piperazine (507.3 mg, 5.068 mmol) was added, and the reaction mixture was stirred for an additional 15 hours. The reaction mixture was diluted with CH$_2$Cl$_2$, washed 3 times with water, dried over MgSO$_4$, filtered, and concentrated to provide a light brown solid (1.449 g, 95%). $[\alpha]_D^{20}$ +110 (c 0.14, CHCl$_3$); $R_f$=0.34 (10% MeOH/CH$_2$Cl$_2$); IR (film) 3369, 2978, 2932, 2243, 1634, 1605 cm$^{-1}$; $^1$H NMR (400 MHz, CDCl$_3$) δ 8.37 (d, J=8.0 Hz, 1H), 8.28 (d, J=8.8 Hz, 1H), 7.80 (d, J=4.8 Hz, 1H), 7.29 (d, J=8.4 Hz, 2H), 7.17 (d, J=8.4 Hz, 2H), 6.95 (d, J=8.4 Hz, 2H), 6.88 (d, J=8.4 Hz, 2H), 6.62 (dd, J=8.8, 2.0 Hz, 1H), 6.46 (d, J=2.0 Hz, 1H), 6.15 (br s, 1H), 5.77 (dd, J=7.6, 2.0 Hz, 1H), 5.10 (dd, J=8.8, 2.4 Hz, 1H), 4.66 (qq, J=6.0, 6.0 Hz, 1H), 4.15 (d, J=2.4 Hz, 2H), 3.86 (s, 3H), 3.73 (ddd, J=13.2, 5.6, 4.4 Hz, 1H), 3.60 (ddd, J=13.2, 6.4, 4.4 Hz, 1H), 3.46-3.35 (m, 2H), 1.20 (d, J=6.0 Hz, 3H), 1.14 (d, J=6.0 Hz, 3H); $^{13}$C NMR (100 MHz, CDCl$_3$) ppm 168.0, 167.0, 163.0, 157.2, 155.9, 136.7, 136.6, 134.3, 133.8, 133.2, 129.4, 128.6, 128.4, 128.0, 113.5, 105.4, 100.3, 71.4, 61.6, 57.5, 55.5, 47.4, 40.9, 39.9, 21.9, 21.5; HRMS (CI): Exact mass calcd for C$_{30}$H$_{33}$Cl$_2$N$_4$O$_5$[M+H]$^+$ 599.1823. found 599.1814.

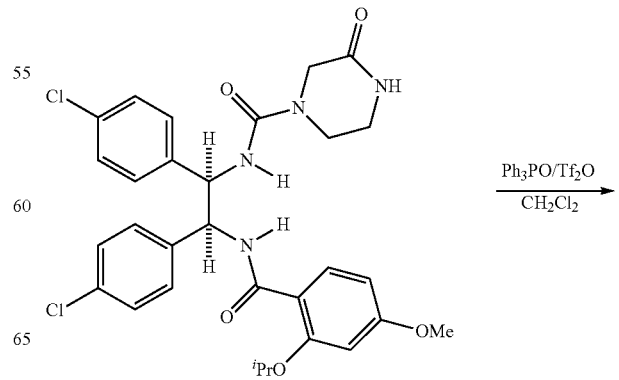

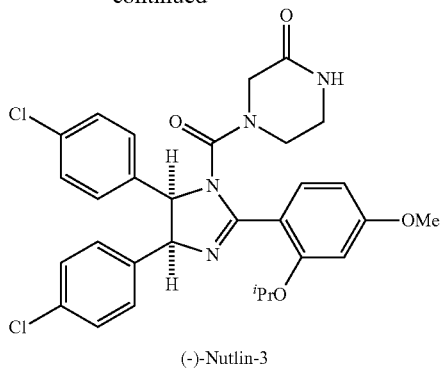

(−)-Nutlin-3

(−)-NUTLIN-3. See Pemberton et al., 2008, which is incorporated herein by reference. Tf$_2$O (280.6 μL, 1.668 mmol) was added to a stirred solution of Ph$_3$PO (928.3 mg, 3.336 mmol) in CH$_2$Cl$_2$ (8 mL) at 0° C. The mixture was stirred for 10 min before urea (50.0 mg, 83.4 μmol) was added, and the reaction was stirred for 3 h at 0° C. The reaction mixture was allowed to warm to room temperature before addition of aq. NaHCO$_3$. The organic layer was separated, the aqueous layer was extracted with CH$_2$Cl$_2$, and the combined organic layers were then dried over MgSO$_4$, filtered, and concentrated. Column chromatography (0-4% methanol in dichloromethane) of the residue provided the compound as a white solid (383.3 mg, 79%). Mp 127.0-129.0° C.; $[\alpha]_D^{20}$ −150 (c 0.13, CHCl$_3$); R$_f$=0.24 (5% MeOH/CH$_2$Cl$_2$); IR (film) 3229, 2980, 2935, 2247, 1678, 1608 cm$^{-1}$; $^1$H NMR (400 MHz, CDCl$_3$) δ 7.59 (d, J=8.8 Hz, 1H), 7.08 (d, J=8.4 Hz, 2H), 7.02 (d, J=8.0 Hz, 2H), 6.92 (d, J=8.4 Hz, 2H), 6.86 (d, J=8.4 Hz, 2H), 6.66 (s, 1H), 6.54 (dd, J=8.4, 1.6 Hz, 1H), 6.47 (br s, 1H), 5.55 (d, J=9.6 Hz, 1H), 5.47 (d, J=9.6 Hz, 1H), 4.60 (qq, J=6.0, 6.0 Hz, 1H), 3.83 (s, 3H), 3.75 (d, J=18.0 Hz, 1H), 3.62 (d, J=18.0 Hz, 1H), 3.40-3.31 (m, 1H), 3.23-3.13 (m, 1H), 2.97 (br s, 2H), 1.37 (d, J=6.0 Hz, 3H), 1.32 (d, J=6.0 Hz, 3H); $^{13}$C NMR (100 MHz, CDCl$_3$) ppm 166.9, 163.0, 160.2, 157.0, 154.7, 136.0, 135.0, 133.1, 132.8, 132.1, 129.2, 128.4, 128.1, 127.9, 113.4, 104.6, 100.1, 71.7, 70.9, 69.1, 55.5, 49.4, 41.8, 40.3, 20.03, 20.01; HRMS (CI): Exact mass calcd for C$_{30}$H$_{31}$Cl$_2$N$_4$O$_4$ [M+H]$^+$ 581.1717. found 581.1705.

* * *

All of the methods disclosed and claimed herein can be made and executed without undue experimentation in light of the present disclosure. While the methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references to the extent that they provide exemplary procedural or other details supplementary to those set forth herein, are specifically incorporated herein by reference.

U.S. Pat. No. 6,835,371
U.S. Publn. 2005/282803
Adams et al., J. Org. Chem., 63:9932-9934, 1998.
Akiyama et al., Advanced Synth. Catalysis, 348:999-1010, 2006.
Anderson, Practical Process Research & Development, 2000.
Bernardi et al., Tetrahedron, 62:375-380, 2005.
Bond et al., Curr. Cancer Drug Targets, 5:3-8, 2005.
Cardona and Goti, Nat. Chem., 1:269-275, 2009.
Carvajal et al., Cancer Res., 65:1918-1924, 2005.
Davis et al., J. Am. Chem. Soc., 132:2880-2882, 2010.
Davis et al., J. Am. Chem. Soc., 132:2880-2882, 2010.
Faugeroux and Genisson, Curr. Organic Chem., 12:751-773, 2008.
Fini et al., Angew. Chem. Int. Ed., 44:7975-7978, 2005.
Fischer and Lane, Trends Pharmacol. Sci., 25:343-346, 2004.
Fry et al., Methods Enzymol., 399:622-633, 2005.
Fry et al., Protein-Protein Interact., 2nd Ed., 893-906, 2005.
Harris, Proc. Natl. Acad. Sci. USA, 103:1659-1660, 2006.
Hattori et al., J. Org. Chem., 68:2099-108, 2003.
Hendrickson and Hussoin, J. Org. Chem., 52:4137-4139, 1987.
Hendrickson and Hussoin, J. Org. Chem., 54:1144-1149, 1989.
Hendrickson and Schwartzman, Ibid, 16:277-280, 1975.
Kanazawa et al., J. Org. Chem., 59, 1238-1240, 1994.
Kim et al., Aldrichimica Acta, 41:77-88, 2008.
Knudsen et al., J. Am. Chem. Soc., 123:5843-5844, 2001.
Kornblum et al., J. Am. Chem. Soc., 78:1497-1501, 1956.
Kotti et al., Chem. Bio. Drug Des., 67:101-114, 2006.
Lowe et al., Nature, 432:307-315, 2004.
Lucet et al., Angew. Chem. Int. Ed., 37:2580-2627, 1998.
March's Advanced Organic Chemistry: Reactions, Mechanisms, and Structure, 2007.
Marianacci et al., Chem. Europ. J., 13:8338-8351, 2007.
Marques-Lopez et al., Eur. J. Org. Chem., 2401-2420, 2009.
Mortensen and O'Doherty, Chemtracts, 18:555-561, 2005.
Nugent et al., J. Am. Chem. Soc., 126:3418-3419, 2004.
Okino et al., Org. Lett., 6:625-627, 2004.
Palomo et al., J. Am. Chem. Soc., 127:17622-17623, 2005.
Pangborn et al., Organometallics, 15, 1518-20, 1996.
PCT Appln. WO 03/051359
Pemberton et al., Tetrahedron 64:9368-76, 2008.
Petersson et al., J. Org. Chem., 73:4691-4693, 2008.
Petersson et al., Org. Biomol. Chem., 7:739-746, 2009.
Rampalakos and Wulff, Advan. Synthesis Catalysis, 350: 1785-1790, 2008.
Satoh et al., Tetrahedron Lett., 4555, 1969.
Shen and Johnston, Org. Lett., 10:4397-4400, 2008.
Ting and Schaus, Eur. J. Org. Chem., 5797-5815, 2007.
Vassilev et al., Science, 303:844-848, 2004.
Vassilev, Cell Cycle, 3:419-421, 2004.
Vögtle and Goldschmitt, Chemische Berichte, 109:1-40, 1976.
Wagaw et al., J Am. Chem. Soc., 119:8451-8, 1997.
Wang et al., J. Pharm. Biomed. Anal., 45:720-729, 2007.
Westermann, Angew. Chem. Int. Ed., 42:151-153, 2003.
Xu et al., Chem. Europ. J., 12:466-476, 2006.
Yamada et al., Angew. Chem. Int. Ed., 38:3504-3506, 1999.
You and Kelly, Org. Lett., 6:1681-1683, 2004.
You et al., Angewandte Chemie. Intl. Ed., 42:83-85, 2003.

The invention claimed is:
1. A method for the preparation of a compound of Formula III comprising reacting a compound of Formula I:

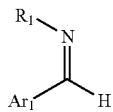 (I)

with a compound of Formula II:

 (II)

in the presence of a catalyst to make a compound of Formula III:

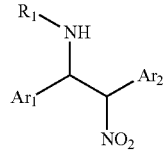 (III)

wherein:
both are p-chlorophenyl; and
$R_1$ is hydrogen, trimethylsilyl, Boc, Fmoc, Cbzacetyl, trifluoroacetyl, benzyl, triphenylmethyl or p-toluenesulfonyl.

2. The method of claim 1, wherein the catalyst is a bis(amidine) and wherein the bis(amidine) is further defined as:

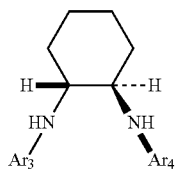

wherein $Ar_3$ and $Ar_4$ are each independently heteroaryl$_{(C \leq 20)}$ or substituted heteroaryl$_{(C \leq 20)}$, provided that at least one of $Ar_3$ and $Ar_4$ comprise at least one nitrogen atom.

3. The method of claim 2, wherein the bis(amidine) is:

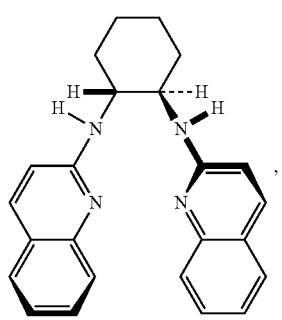

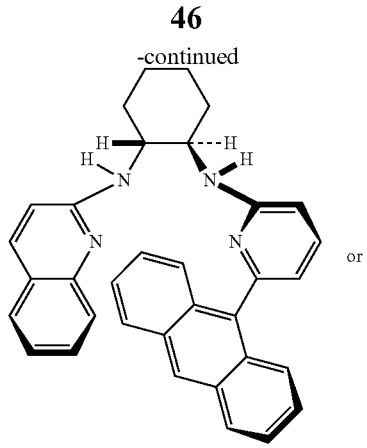

4. The method of claim 2, wherein the bis(amidine) is:

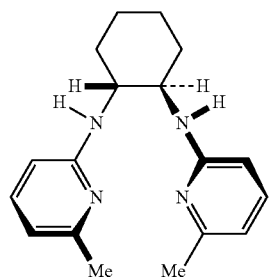

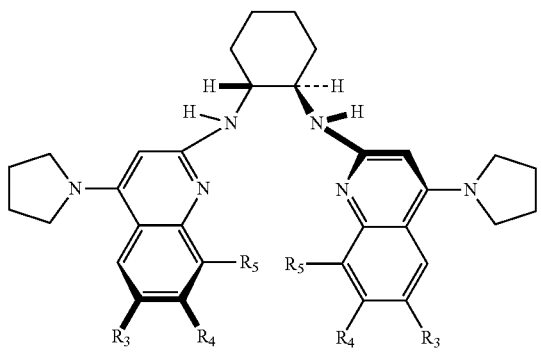

wherein $R_3$, $R_4$ and $R_5$ are each independently:
hydrogen, hydroxy, halo, amino, nitro, or cyano or thio; or alkyl$_{(C \leq 6)}$, acyl$_{(C \leq 6)}$, alkoxy$_{(C \leq 6)}$, acyloxy$_{(C \leq 6)}$, alkylamino$_{(C \leq 6)}$, dialkylamino$_{(C \leq 6)}$, Amido$_{(C \leq 6)}$, or a substituted version of any of these groups.

5. The method of claim 1, wherein one optical isomer of the compound of formula III is made with a diastereomeric ratio (dr) greater than 10:1 and an enantiomer excess (ee) greater than 85% and wherein the optical isomer has the formula IIIa:

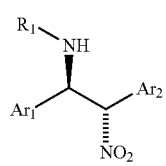 (IIIa)

wherein:
 both are p-chlorophenyl; and
 $R_1$ is hydrogen, trimethylsilyl, Boc, Fmoc, Cbzacetyl, trifluoroacetyl, benzyl, triphenylmethyl or p-toluenesulfonyl.

6. The method of claim 5, wherein the dr is from 12:1 to 100:1.

7. The method of claim 5, wherein the ee is from 90% to 99%.

8. A compound of the formula:

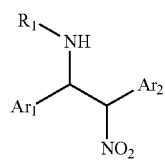
(III)

wherein:
 both are p-chlorophenyl; and
 $R_1$ is hydrogen, trimethylsilyl, Boc, Fmoc, Cbzacetyl, trifluoroacetyl, benzyl, triphenylmethyl or p-toluenesulfonyl.

9. The compound of claim 8, wherein $R_1$ is H.

10. A composition comprising a compound of claim 8, wherein one stereoisomer of the compound of formula III is present with a diastereomeric ratio (dr) from about 10:1 to about 100:1 and an enantiomer excess (ee) from 85% to 100%.

11. The compound of claim 8, which is a stereoisomer of the formula IIIa:

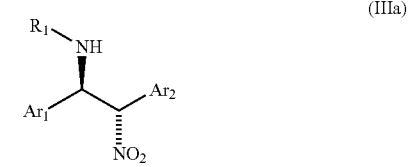
(IIIa)

wherein:
 both are p-chlorophenyl; and
 $R_1$ is Boc, Fmoc, Cbzacetyl, trifluoroacetyl, benzyl, triphenylmethyl or p-toluenesulfonyl.

12. The composition of claim 10, wherein the ee is 90% to 99%.

13. The compound of claim 8, wherein $R_1$ is Boc.

14. The compound of claim 8 further defined as:

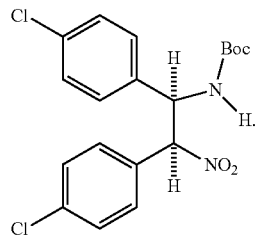

* * * * *

UNITED STATES PATENT AND TRADEMARK OFFICE
CERTIFICATE OF CORRECTION

PATENT NO. : 8,889,863 B2  
APPLICATION NO. : 13/183202  
DATED : November 18, 2014  
INVENTOR(S) : Jeffrey N. Johnston and Tyler A. Davis Page 1 of 1

It is certified that error appears in the above-identified patent and that said Letters Patent is hereby corrected as shown below:

On the Title Page, item (57) Abstract, line 2, delete "are provided".

In the Claims

In claim 1, column 45, line 32, before "both" insert --Ar1 and Ar2--.

In claim 1, column 45, line 33, delete "Cbzacetyl" and insert --Cbz, acetyl-- therefor.

In claim 5, column 47, line 2, before "both" insert --Ar1 and Ar2--.

In claim 5, column 47, line 3, delete "Cbzacetyl" and insert --Cbz, acetyl-- therefor.

In claim 8, column 47, line 21, before "both" insert --Ar1 and Ar2--.

In claim 8, column 47, line 22, delete "Cbzacetyl" and insert --Cbz, acetyl-- therefor.

In claim 11, column 48, line 12, before "both" insert --Ar1 and Ar2--.

In claim 11, column 48, line 13, delete "Cbzacetyl" and insert --Cbz, acetyl-- therefor.

Signed and Sealed this  
Tenth Day of March, 2015

Michelle K. Lee  
*Deputy Director of the United States Patent and Trademark Office*